US010198966B2

(12) United States Patent
Wachli et al.

(10) Patent No.: US 10,198,966 B2
(45) Date of Patent: Feb. 5, 2019

(54) ADVANCED FIRST ENTRY MODEL FOR SURGICAL SIMULATION

(71) Applicant: Applied Medical Resources Corporation, Rancho Santa Margarita, CA (US)

(72) Inventors: Serene Wachli, Rancho Santa Margarita, CA (US); Gregory K. Hofstetter, Rancho Santa Margarita, CA (US); Katie Black, Rancho Santa Margarita, CA (US); Nikolai Poulsen, Rancho Santa Margarita, CA (US); Heidi Holmes, Rancho Santa Margarita, CA (US); Natasha Felsinger, Rancho Santa Margarita, CA (US); Tracy Breslin, Rancho Santa Margarita, CA (US); Kennii Pravongviengkham, Rancho Santa Margarita, CA (US); Boun Pravong, Rancho Santa Margarita, CA (US); Eduardo Bolanos, Rancho Santa Margarita, CA (US); Zoran Falkenstein, Rancho Santa Margarita, CA (US); Charles C. Hart, Rancho Santa Margarita, CA (US); Tina Talwar, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 462 days.

(21) Appl. No.: 14/657,925

(22) Filed: Mar. 13, 2015

(65) Prior Publication Data
US 2015/0187229 A1    Jul. 2, 2015

Related U.S. Application Data

(63) Continuation-in-part of application No. 14/340,234, filed on Jul. 24, 2014, now Pat. No. 9,548,002.
(Continued)

(51) Int. Cl.
*G09B 23/30* (2006.01)
*G09B 23/28* (2006.01)

(52) U.S. Cl.
CPC ................. *G09B 23/285* (2013.01)

(58) Field of Classification Search
CPC ......... G09B 23/285; G09B 19/00; G09B 5/02
(Continued)

(56) References Cited

U.S. PATENT DOCUMENTS

| 184,573 A | 11/1876 | Becker |
| 2,127,774 A | 8/1938 | Jacobson |

(Continued)

FOREIGN PATENT DOCUMENTS

| CN | 2421706 Y | 2/2001 |
| CN | 2751372 Y | 1/2006 |

(Continued)

OTHER PUBLICATIONS

De Keulenaer, B. L., De Waele, J. J., Powel, B., Malbrain, M. L. N. G., What is normal intra-abdominal pressure and how is it affected by positioning, body mass and positive end- expiratory pressure?, Springer- Verlag, Feb. 26, 3009, p. 6.*
(Continued)

*Primary Examiner* — Sam Yao
*Assistant Examiner* — Lily M Del Valle
(74) *Attorney, Agent, or Firm* — Cynthia A. Bonner

(57) ABSTRACT

The present invention provides a surgical training device for training laparoscopic first entry surgical techniques. The
(Continued)

training device includes a simulated abdominal wall that is penetrable with an optical trocar. A receptacle containing a tissue simulation is located inside the receptacle. The tissue simulation is observable via scope placed inside the optical trocar. Upon penetration of the one or more of the simulated abdominal wall and receptacle, the tissue simulation appears to translate distally relative to the simulated abdominal wall. The distal translation is effected by a variety of ways including the release of negative pressure inside the receptacle upon penetration and the expansion of an elastic wall of the receptacle with the introduction of fluid under pressure into the receptacle.

19 Claims, 6 Drawing Sheets

Related U.S. Application Data

(60) Provisional application No. 61/971,714, filed on Mar. 28, 2014, provisional application No. 61/952,289, filed on Mar. 13, 2014, provisional application No. 61/857,982, filed on Jul. 24, 2013.

(58) Field of Classification Search
USPC .......................................................... 434/272
See application file for complete search history.

(56) References Cited

U.S. PATENT DOCUMENTS

| | | |
|---|---|---|
| 2,284,888 A | 6/1942 | Arnell, Jr. |
| 2,324,702 A | 7/1943 | Hoffman et al. |
| 2,345,489 A | 3/1944 | Lord |
| 2,495,568 A | 1/1950 | Coel |
| 3,766,666 A | 10/1973 | Stroop |
| 3,775,865 A | 12/1973 | Rowan |
| 3,789,518 A | 2/1974 | Chase |
| 3,921,311 A | 11/1975 | Beasley et al. |
| 3,991,490 A | 11/1976 | Markman |
| 4,001,951 A | 1/1977 | Fasse |
| 4,001,952 A | 1/1977 | Kleppinger |
| 4,321,047 A | 3/1982 | Landis |
| 4,323,350 A | 4/1982 | Bowden, Jr. |
| 4,332,569 A | 6/1982 | Burbank |
| 4,371,345 A | 2/1983 | Palmer et al. |
| 4,386,917 A | 6/1983 | Forrest |
| 4,459,113 A | 7/1984 | Boscaro Gatti et al. |
| 4,481,001 A | 11/1984 | Graham et al. |
| 4,596,528 A | 6/1986 | Lewis et al. |
| 4,726,772 A | 2/1988 | Amplatz |
| 4,737,109 A | 4/1988 | Abramson |
| 4,789,340 A | 12/1988 | Zikria |
| 4,832,978 A | 5/1989 | Lesser |
| 4,867,686 A | 9/1989 | Goldstein |
| 4,907,973 A | 3/1990 | Hon |
| 4,938,696 A | 7/1990 | Foster et al. |
| 4,940,412 A | 7/1990 | Blumenthal |
| 5,061,187 A | 10/1991 | Jerath |
| 5,083,962 A | 1/1992 | Pracas |
| 5,104,328 A | 4/1992 | Lounsbury |
| 5,149,270 A | 9/1992 | McKeown |
| 5,180,308 A | 1/1993 | Garito et al. |
| 5,230,630 A | 7/1993 | Burgett |
| 5,273,435 A | 12/1993 | Jacobson |
| 5,295,694 A | 3/1994 | Levin |
| 5,310,348 A | 5/1994 | Miller |
| 5,318,448 A | 6/1994 | Garito et al. |
| 5,320,537 A | 6/1994 | Watson |
| 5,358,408 A | 10/1994 | Medina |
| 5,368,487 A | 11/1994 | Medina |
| 5,380,207 A | 1/1995 | Siepser |
| 5,403,191 A | 4/1995 | Tuason |
| 5,425,644 A | 6/1995 | Szinicz |
| 5,425,731 A | 6/1995 | Daniel et al. |
| 5,472,345 A | 12/1995 | Eggert |
| 5,518,406 A | 5/1996 | Waters |
| 5,518,407 A | 5/1996 | Greenfield et al. |
| 5,520,633 A | 5/1996 | Costin |
| 5,541,304 A | 7/1996 | Thompson |
| 5,599,297 A * | 2/1997 | Chin ................. A61M 13/003 604/26 |
| 5,620,326 A | 4/1997 | Younker |
| 5,720,742 A | 2/1998 | Zacharias |
| 5,722,836 A | 3/1998 | Younker |
| 5,727,948 A | 3/1998 | Jordan |
| 5,743,730 A | 4/1998 | Clester et al. |
| 5,762,458 A | 6/1998 | Wang et al. |
| 5,769,640 A | 6/1998 | Jacobus et al. |
| 5,775,916 A | 7/1998 | Cooper et al. |
| 5,785,531 A | 7/1998 | Leung |
| 5,800,178 A | 9/1998 | Gillio |
| 5,803,746 A | 9/1998 | Barrie et al. |
| 5,807,378 A | 9/1998 | Jensen et al. |
| 5,810,880 A | 9/1998 | Jensen et al. |
| 5,814,038 A | 9/1998 | Jensen et al. |
| 5,850,033 A | 12/1998 | Mirzeabasov et al. |
| 5,855,583 A | 1/1999 | Wang et al. |
| 5,873,732 A | 2/1999 | Hasson |
| 5,873,863 A | 2/1999 | Komlosi |
| 5,908,302 A | 6/1999 | Goldfarb |
| 5,947,743 A | 9/1999 | Hasson |
| 5,951,301 A | 9/1999 | Younker |
| 6,080,181 A | 6/2000 | Jensen et al. |
| 6,083,008 A | 7/2000 | Yamada et al. |
| 6,113,395 A | 9/2000 | Hon |
| 6,234,804 B1 | 5/2001 | Yong |
| 6,336,812 B1 | 1/2002 | Cooper et al. |
| 6,398,557 B1 | 6/2002 | Hoballah |
| 6,413,264 B1 | 7/2002 | Jensen et al. |
| 6,474,993 B1 | 11/2002 | Grund et al. |
| 6,485,308 B1 | 11/2002 | Goldstein |
| 6,488,507 B1 | 12/2002 | Stoloff et al. |
| 6,497,902 B1 | 12/2002 | Ma |
| 6,511,325 B1 | 1/2003 | Lalka et al. |
| 6,517,354 B1 | 2/2003 | Levy |
| 6,568,941 B1 | 5/2003 | Goldstein |
| 6,620,174 B2 | 9/2003 | Jensen et al. |
| 6,654,000 B2 | 11/2003 | Rosenberg |
| 6,659,776 B1 * | 12/2003 | Aumann ............... G09B 23/285 434/262 |
| 6,773,263 B2 | 8/2004 | Nicholls et al. |
| 6,780,016 B1 * | 8/2004 | Toly ..................... G09B 23/285 434/262 |
| 6,817,973 B2 | 11/2004 | Merril et al. |
| 6,820,025 B2 | 11/2004 | Bachmann et al. |
| 6,854,976 B1 | 2/2005 | Suhr |
| 6,857,878 B1 | 2/2005 | Chosack et al. |
| 6,863,536 B1 | 3/2005 | Fisher et al. |
| 6,866,514 B2 | 3/2005 | Von Roeschlaub et al. |
| 6,887,082 B2 | 5/2005 | Shun |
| 6,929,481 B1 | 8/2005 | Alexander et al. |
| 6,939,138 B2 | 9/2005 | Chosack et al. |
| 6,950,025 B1 | 9/2005 | Nguyen |
| 6,960,617 B2 | 11/2005 | Omidian et al. |
| 6,997,719 B2 | 2/2006 | Wellman et al. |
| 7,008,232 B2 | 3/2006 | Brassel |
| 7,018,327 B1 | 3/2006 | Conti |
| 7,025,064 B2 | 4/2006 | Wang et al. |
| 7,056,123 B2 | 6/2006 | Gregorio et al. |
| 7,080,984 B1 | 7/2006 | Cohen |
| 7,118,582 B1 | 10/2006 | Wang et al. |
| 7,255,565 B2 | 8/2007 | Keegan |
| 7,269,532 B2 | 9/2007 | David et al. |
| 7,272,766 B2 | 9/2007 | Sakezles |
| 7,300,450 B2 | 11/2007 | Vleugels et al. |
| 7,364,582 B2 | 4/2008 | Lee |
| 7,404,716 B2 | 7/2008 | Gregorio et al. |
| 7,419,376 B2 | 9/2008 | Sarvazyan et al. |
| 7,427,199 B2 | 9/2008 | Sakezles |
| 7,431,189 B2 | 10/2008 | Shelton, IV et al. |
| 7,441,684 B2 | 10/2008 | Shelton, IV et al. |
| 7,465,168 B2 | 12/2008 | Allen et al. |

(56) References Cited

U.S. PATENT DOCUMENTS

| | | | |
|---|---|---|---|
| 7,467,075 B2 | 12/2008 | Humphries et al. |
| 7,544,062 B1 | 6/2009 | Hauschild et al. |
| 7,549,866 B2 | 6/2009 | Cohen et al. |
| 7,553,159 B1 | 6/2009 | Arnal et al. |
| 7,575,434 B2 | 8/2009 | Palakodeti |
| 7,594,815 B2 | 9/2009 | Toly |
| 7,621,749 B2 | 11/2009 | Munday |
| 7,646,901 B2 | 1/2010 | Murphy et al. |
| 7,648,367 B1 | 1/2010 | Makower et al. |
| 7,648,513 B2 | 1/2010 | Green et al. |
| 7,651,332 B2 | 1/2010 | Dupuis et al. |
| 7,677,897 B2 | 3/2010 | Sakezles |
| 7,775,916 B1 | 8/2010 | Mahoney |
| 7,780,451 B2 | 8/2010 | Willobee et al. |
| 7,802,990 B2 | 9/2010 | Korndorffer et al. |
| 7,803,151 B2 | 9/2010 | Whitman |
| 7,806,696 B2 | 10/2010 | Alexander et al. |
| 7,819,799 B2 | 10/2010 | Merril et al. |
| 7,833,018 B2 | 11/2010 | Alexander et al. |
| 7,837,473 B2 | 11/2010 | Koh |
| 7,850,454 B2 | 12/2010 | Toly |
| 7,850,456 B2 | 12/2010 | Chosack et al. |
| 7,854,612 B2 | 12/2010 | Frassica et al. |
| 7,857,626 B2 | 12/2010 | Toly |
| 7,866,983 B2 | 1/2011 | Hemphill et al. |
| 7,931,470 B2 | 4/2011 | Alexander et al. |
| 7,931,471 B2 | 4/2011 | Senagore et al. |
| 7,988,992 B2 | 8/2011 | Omidian et al. |
| 7,993,140 B2 | 8/2011 | Sakezles |
| 7,997,903 B2 | 8/2011 | Hasson et al. |
| 8,007,281 B2 | 8/2011 | Toly |
| 8,007,282 B2 | 8/2011 | Gregorio et al. |
| 8,016,818 B2 | 9/2011 | Ellis et al. |
| 8,021,162 B2 | 9/2011 | Sui |
| 8,048,088 B2 | 11/2011 | Green et al. |
| 8,083,691 B2 | 12/2011 | Goldenberg et al. |
| 8,116,847 B2 | 2/2012 | Gattani et al. |
| 8,137,110 B2 | 3/2012 | Sakezles |
| 8,157,145 B2 | 4/2012 | Shelton, IV et al. |
| 8,197,464 B2 | 6/2012 | Krever et al. |
| 8,205,779 B2 | 6/2012 | Ma et al. |
| 8,221,129 B2 | 7/2012 | Parry et al. |
| 8,297,982 B2 | 10/2012 | Park et al. |
| 8,308,817 B2 | 11/2012 | Egilsson et al. |
| 8,323,028 B2 | 12/2012 | Matanhelia |
| 8,323,029 B2 | 12/2012 | Toly |
| 8,328,560 B2 | 12/2012 | Niblock et al. |
| 8,342,851 B1 | 1/2013 | Speeg et al. |
| 8,403,674 B2 | 3/2013 | Feygin et al. |
| 8,403,675 B2 | 3/2013 | Stoianovici et al. |
| 8,403,676 B2 | 3/2013 | Frassica et al. |
| 8,408,920 B2 | 4/2013 | Speller |
| 8,425,234 B2 | 4/2013 | Sakezles |
| 8,439,687 B1 | 5/2013 | Morriss et al. |
| 8,442,621 B2 | 5/2013 | Gorek et al. |
| 8,454,368 B2 | 6/2013 | Ault et al. |
| 8,459,094 B2 | 6/2013 | Yanni |
| 8,459,520 B2 | 6/2013 | Giordano et al. |
| 8,460,002 B2 | 6/2013 | Wang et al. |
| 8,469,715 B2 | 6/2013 | Ambrozio |
| 8,469,716 B2 | 6/2013 | Fedotov et al. |
| 8,480,407 B2 | 7/2013 | Campbell et al. |
| 8,480,408 B2 | 7/2013 | Ishii et al. |
| 8,491,309 B2 | 7/2013 | Parry et al. |
| 8,500,753 B2 | 8/2013 | Green et al. |
| 8,512,044 B2 | 8/2013 | Sakezles |
| 8,517,243 B2 | 8/2013 | Giordano et al. |
| 8,521,252 B2 | 8/2013 | Diez |
| 8,535,062 B2 | 9/2013 | Nguyen |
| 8,544,711 B2 | 10/2013 | Ma et al. |
| 8,556,635 B2 | 10/2013 | Toly |
| 8,608,483 B2 | 12/2013 | Trotta et al. |
| 8,613,621 B2 | 12/2013 | Henderickson et al. |
| 8,636,520 B2 | 1/2014 | Iwasaki et al. |
| D699,297 S | 2/2014 | Bahsoun et al. |
| 8,641,423 B2 | 2/2014 | Gumkowski |
| 8,647,125 B2 | 2/2014 | Johns et al. |
| 8,678,831 B2 | 3/2014 | Trotta et al. |
| 8,679,279 B2 | 3/2014 | Thompson et al. |
| 8,696,363 B2 | 4/2014 | Gray et al. |
| 8,708,213 B2 | 4/2014 | Shelton, IV et al. |
| 8,708,707 B2 | 4/2014 | Hendrickson et al. |
| 8,764,449 B2 | 7/2014 | Rios et al. |
| 8,764,452 B2 | 7/2014 | Pravong et al. |
| 8,800,839 B2 | 8/2014 | Beetel |
| 8,801,437 B2 | 8/2014 | Mousques |
| 8,801,438 B2 | 8/2014 | Sakezles |
| 8,807,414 B2 | 8/2014 | Ross et al. |
| 8,808,004 B2 | 8/2014 | Misawa et al. |
| 8,808,311 B2 | 8/2014 | Heinrich et al. |
| 8,814,573 B2 | 8/2014 | Nguyen |
| 8,827,988 B2 | 9/2014 | Belson et al. |
| 8,840,628 B2 | 9/2014 | Green et al. |
| 8,870,576 B2 | 10/2014 | Millon et al. |
| 8,888,498 B2 | 11/2014 | Bisaillon et al. |
| 8,893,946 B2 | 11/2014 | Boudreaux et al. |
| 8,911,238 B2 | 12/2014 | Forsythe |
| 8,915,742 B2 | 12/2014 | Hendrickson et al. |
| 8,940,009 B2 * | 1/2015 | Kahle ............... A61B 17/3417 |
| | | 604/264 |
| 8,945,095 B2 | 2/2015 | Blumenkranz et al. |
| 8,961,190 B2 | 2/2015 | Hart et al. |
| 8,966,954 B2 | 3/2015 | Ni et al. |
| 8,968,003 B2 | 3/2015 | Hendrickson et al. |
| 9,008,989 B2 | 4/2015 | Wilson et al. |
| 9,011,366 B2 * | 4/2015 | Dean ..................... A61B 18/00 |
| | | 604/131 |
| 9,017,080 B1 | 4/2015 | Placik |
| 9,026,247 B2 | 5/2015 | White |
| 9,050,201 B2 | 6/2015 | Egilsson et al. |
| 9,056,126 B2 | 6/2015 | Hersel et al. |
| 9,070,306 B2 | 6/2015 | Rappel et al. |
| 9,087,458 B2 | 7/2015 | Shim et al. |
| 9,117,377 B2 | 8/2015 | Shim et al. |
| 9,119,572 B2 | 9/2015 | Gorek et al. |
| 9,123,261 B2 | 9/2015 | Lowe |
| 9,129,054 B2 | 9/2015 | Nawana et al. |
| 9,196,176 B2 | 11/2015 | Hager et al. |
| 9,226,799 B2 | 1/2016 | Lightcap et al. |
| 9,257,055 B2 | 2/2016 | Endo et al. |
| 9,265,587 B2 | 2/2016 | Vancamberg et al. |
| 9,295,468 B2 | 3/2016 | Heinrich et al. |
| 9,351,714 B2 | 5/2016 | Ross et al. |
| 9,336,694 B2 | 6/2016 | Shim et al. |
| 9,358,682 B2 | 6/2016 | Ruiz Morales |
| 9,364,224 B2 | 6/2016 | Nicholas et al. |
| 9,364,279 B2 | 6/2016 | Houser et al. |
| 9,370,361 B2 | 6/2016 | Viola et al. |
| 9,373,270 B2 | 6/2016 | Miyazaki |
| 9,439,649 B2 | 9/2016 | Shelton, IV et al. |
| 9,439,733 B2 | 9/2016 | Ha et al. |
| 9,449,532 B2 | 9/2016 | Black et al. |
| 9,468,438 B2 | 10/2016 | Baber et al. |
| 2001/0019818 A1 | 9/2001 | Yong |
| 2002/0168619 A1 | 11/2002 | Provenza |
| 2003/0031993 A1 | 2/2003 | Pugh |
| 2003/0091967 A1 | 5/2003 | Chosack et al. |
| 2003/0176770 A1 | 9/2003 | Merril et al. |
| 2004/0005423 A1 | 1/2004 | Dalton et al. |
| 2004/0248072 A1 | 12/2004 | Gray et al. |
| 2005/0008997 A1 | 1/2005 | Herman |
| 2005/0026125 A1 | 2/2005 | Toly |
| 2005/0084833 A1 | 4/2005 | Lacey et al. |
| 2005/0131390 A1 | 6/2005 | Heinrich et al. |
| 2005/0142525 A1 | 6/2005 | Cotin et al. |
| 2005/0192595 A1 | 9/2005 | Green et al. |
| 2005/0196739 A1 | 9/2005 | Moriyama |
| 2005/0196740 A1 | 9/2005 | Moriyana |
| 2005/0214727 A1 * | 9/2005 | Stoianovici ............ G09B 23/28 |
| | | 434/262 |
| 2006/0046235 A1 | 3/2006 | Alexander et al. |
| 2006/0252019 A1 | 11/2006 | Burkitt et al. |
| 2006/0275741 A1 | 12/2006 | Chewning et al. |
| 2007/0074584 A1 | 4/2007 | Talarico et al. |

(56) References Cited

U.S. PATENT DOCUMENTS

| | | |
|---|---|---|
| 2007/0077544 A1 | 4/2007 | Lemperle et al. |
| 2007/0078484 A1 | 4/2007 | Talarico et al. |
| 2007/0148626 A1 | 6/2007 | Ikeda |
| 2007/0166682 A1 | 7/2007 | Yarin et al. |
| 2007/0197895 A1 | 8/2007 | Nycz et al. |
| 2007/0225734 A1 | 9/2007 | Bell et al. |
| 2007/0275359 A1 | 11/2007 | Rotnes et al. |
| 2008/0032272 A1 | 2/2008 | Palakodeti |
| 2008/0032273 A1 | 2/2008 | Macnamara et al. |
| 2008/0052034 A1 | 2/2008 | David et al. |
| 2008/0064017 A1 | 3/2008 | Grundmeyer, III |
| 2008/0076101 A1 | 3/2008 | Hyde et al. |
| 2008/0097501 A1 | 4/2008 | Blier |
| 2008/0108869 A1 | 5/2008 | Sanders et al. |
| 2008/0187895 A1 | 8/2008 | Sakezles |
| 2008/0188948 A1 | 8/2008 | Flatt |
| 2008/0299529 A1 | 12/2008 | Schaller |
| 2009/0068627 A1 | 3/2009 | Toly |
| 2009/0142739 A1* | 6/2009 | Wang .................. G09B 23/285 434/262 |
| 2009/0142741 A1 | 6/2009 | Ault et al. |
| 2009/0143642 A1 | 6/2009 | Takahashi et al. |
| 2009/0176196 A1 | 7/2009 | Niblock et al. |
| 2009/0187079 A1 | 7/2009 | Albrecht et al. |
| 2009/0246747 A1 | 10/2009 | Buckman, Jr. |
| 2009/0298034 A1 | 12/2009 | Parry et al. |
| 2010/0004599 A1* | 1/2010 | Zhou .................. A61B 17/3421 604/167.04 |
| 2010/0007599 A1* | 1/2010 | Kerofsky ............. G09G 3/3413 345/102 |
| 2010/0047752 A1 | 2/2010 | Chan et al. |
| 2010/0094312 A1 | 4/2010 | Ruiz Morales et al. |
| 2010/0094730 A1 | 4/2010 | Di Betta et al. |
| 2010/0099067 A1 | 4/2010 | Agro |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1 | 7/2010 | Ryan et al. |
| 2010/0167254 A1 | 7/2010 | Nguyen |
| 2010/0196867 A1 | 8/2010 | Geerligs et al. |
| 2010/0204713 A1 | 8/2010 | Ruiz Morales |
| 2010/0209899 A1 | 8/2010 | Park |
| 2010/0258611 A1 | 10/2010 | Smith et al. |
| 2010/0273136 A1 | 10/2010 | Kandasami et al. |
| 2010/0279263 A1 | 11/2010 | Duryea |
| 2010/0324541 A1 | 12/2010 | Whitman |
| 2011/0046637 A1 | 2/2011 | Patel et al. |
| 2011/0046659 A1 | 2/2011 | Ramstein et al. |
| 2011/0087238 A1 | 4/2011 | Wang et al. |
| 2011/0091855 A1 | 4/2011 | Miyazaki |
| 2011/0137337 A1 | 6/2011 | van den Dool et al. |
| 2011/0200976 A1 | 8/2011 | Hou et al. |
| 2011/0207104 A1 | 8/2011 | Trotta |
| 2011/0208238 A1* | 8/2011 | Hoffman .......... A61B 17/00491 606/213 |
| 2011/0218550 A1 | 9/2011 | Ma |
| 2011/0244436 A1 | 10/2011 | Campo |
| 2011/0269109 A2 | 11/2011 | Miyazaki |
| 2011/0281251 A1 | 11/2011 | Mousques |
| 2011/0301620 A1 | 12/2011 | Di Betta et al. |
| 2012/0015337 A1 | 1/2012 | Hendrickson et al. |
| 2012/0015339 A1 | 1/2012 | Hendrickson et al. |
| 2012/0016362 A1 | 1/2012 | Heinrich et al. |
| 2012/0028231 A1 | 2/2012 | Misawa et al. |
| 2012/0045743 A1 | 2/2012 | Misawa et al. |
| 2012/0065632 A1 | 3/2012 | Shadduck |
| 2012/0082970 A1 | 4/2012 | Pravong et al. |
| 2012/0100217 A1 | 4/2012 | Green et al. |
| 2012/0115117 A1 | 5/2012 | Marshall |
| 2012/0115118 A1 | 5/2012 | Marshall |
| 2012/0116391 A1 | 5/2012 | Houser et al. |
| 2012/0148994 A1 | 6/2012 | Hori et al. |
| 2012/0164616 A1 | 6/2012 | Endo et al. |
| 2012/0165866 A1 | 6/2012 | Kaiser et al. |
| 2012/0172873 A1 | 7/2012 | Artale et al. |
| 2012/0179072 A1 | 7/2012 | Kegreiss |
| 2012/0202180 A1 | 8/2012 | Stock et al. |
| 2012/0264096 A1 | 10/2012 | Taylor et al. |
| 2012/0264097 A1 | 10/2012 | Newcott et al. |
| 2012/0282583 A1 | 11/2012 | Thaler et al. |
| 2012/0282584 A1 | 11/2012 | Millon et al. |
| 2012/0283707 A1 | 11/2012 | Giordano et al. |
| 2012/0288839 A1 | 11/2012 | Crabtree |
| 2012/0308977 A1 | 12/2012 | Tortola |
| 2013/0087597 A1 | 4/2013 | Shelton, IV et al. |
| 2013/0101973 A1 | 4/2013 | Hoke et al. |
| 2013/0105552 A1 | 5/2013 | Weir et al. |
| 2013/0116668 A1 | 5/2013 | Shelton, IV et al. |
| 2013/0157240 A1 | 6/2013 | Hart et al. |
| 2013/0171288 A1 | 7/2013 | Harders |
| 2013/0177890 A1 | 7/2013 | Sakezles |
| 2013/0192741 A1 | 8/2013 | Trotta et al. |
| 2013/0218166 A1 | 8/2013 | Elmore |
| 2013/0224709 A1 | 8/2013 | Riojas et al. |
| 2013/0245681 A1 | 9/2013 | Straehnz et al. |
| 2013/0253480 A1 | 9/2013 | Kimball et al. |
| 2013/0267876 A1 | 10/2013 | Leckenby et al. |
| 2013/0282038 A1 | 10/2013 | Dannaher et al. |
| 2013/0288216 A1 | 10/2013 | Parry, Jr. et al. |
| 2013/0302771 A1 | 11/2013 | Alderete |
| 2013/0324991 A1 | 12/2013 | Clem et al. |
| 2013/0324999 A1 | 12/2013 | Price et al. |
| 2014/0011172 A1 | 1/2014 | Lowe |
| 2014/0017651 A1 | 1/2014 | Sugimoto et al. |
| 2014/0030682 A1 | 1/2014 | Thilenius |
| 2014/0038151 A1 | 2/2014 | Hart |
| 2014/0051049 A1 | 2/2014 | Jarc et al. |
| 2014/0072941 A1 | 3/2014 | Hendrickson et al. |
| 2014/0087345 A1 | 3/2014 | Breslin et al. |
| 2014/0087346 A1 | 3/2014 | Breslin et al. |
| 2014/0087347 A1 | 3/2014 | Tracy et al. |
| 2014/0087348 A1 | 3/2014 | Tracy et al. |
| 2014/0088413 A1 | 3/2014 | Von Bucsh et al. |
| 2014/0093852 A1 | 4/2014 | Poulsen et al. |
| 2014/0093854 A1 | 4/2014 | Poulsen et al. |
| 2014/0099858 A1 | 4/2014 | Hernandez |
| 2014/0106328 A1 | 4/2014 | Loor |
| 2014/0107471 A1 | 4/2014 | Haider et al. |
| 2014/0156002 A1 | 6/2014 | Thompson et al. |
| 2014/0162016 A1 | 6/2014 | Matsui et al. |
| 2014/0170623 A1 | 6/2014 | Jarstad et al. |
| 2014/0186809 A1 | 7/2014 | Hendrickson et al. |
| 2014/0200561 A1 | 7/2014 | Ingmanson et al. |
| 2014/0212861 A1 | 7/2014 | Romano |
| 2014/0220527 A1 | 8/2014 | Li et al. |
| 2014/0220530 A1 | 8/2014 | Merkle et al. |
| 2014/0220532 A1 | 8/2014 | Ghez et al. |
| 2014/0242564 A1 | 8/2014 | Pravong et al. |
| 2014/0246479 A1 | 9/2014 | Baber et al. |
| 2014/0248596 A1 | 9/2014 | Hart et al. |
| 2014/0263538 A1 | 9/2014 | Leimbach et al. |
| 2014/0272878 A1 | 9/2014 | Shim et al. |
| 2014/0272879 A1 | 9/2014 | Shim et al. |
| 2014/0275795 A1 | 9/2014 | Little et al. |
| 2014/0275981 A1 | 9/2014 | Selover et al. |
| 2014/0277017 A1 | 9/2014 | Leimbach et al. |
| 2014/0303643 A1 | 10/2014 | Ha et al. |
| 2014/0303646 A1 | 10/2014 | Morgan et al. |
| 2014/0303660 A1 | 10/2014 | Boyden et al. |
| 2014/0308643 A1 | 10/2014 | Trotta et al. |
| 2014/0342334 A1 | 11/2014 | Black et al. |
| 2014/0349266 A1 | 11/2014 | Choi |
| 2014/0350530 A1 | 11/2014 | Ross et al. |
| 2014/0357977 A1 | 12/2014 | Zhou |
| 2014/0370477 A1 | 12/2014 | Black et al. |
| 2014/0371761 A1 | 12/2014 | Juanpera |
| 2014/0378995 A1 | 12/2014 | Kumar et al. |
| 2015/0031008 A1 | 1/2015 | Black et al. |
| 2015/0037773 A1 | 2/2015 | Quirarte Catano |
| 2015/0038613 A1 | 2/2015 | Sun et al. |
| 2015/0076207 A1 | 3/2015 | Boudreaux et al. |
| 2015/0086955 A1 | 3/2015 | Poniatowski et al. |
| 2015/0132732 A1 | 5/2015 | Hart et al. |
| 2015/0132733 A1 | 5/2015 | Garvik et al. |

(56) References Cited

U.S. PATENT DOCUMENTS

| | | |
|---|---|---|
| 2015/0135832 A1 | 5/2015 | Blumenkranz et al. |
| 2015/0148660 A1 | 5/2015 | Weiss et al. |
| 2015/0164598 A1 | 6/2015 | Blumenkranz et al. |
| 2015/0187229 A1 | 7/2015 | Wachli et al. |
| 2015/0194075 A1 | 7/2015 | Rappel et al. |
| 2015/0202299 A1 | 7/2015 | Burdick et al. |
| 2015/0209035 A1 | 7/2015 | Zemlock |
| 2015/0209059 A1 | 7/2015 | Trees et al. |
| 2015/0209573 A1 | 7/2015 | Hibner et al. |
| 2015/0228206 A1 | 8/2015 | Shim et al. |
| 2015/0262511 A1 | 9/2015 | Lin et al. |
| 2015/0265431 A1 | 9/2015 | Egilsson et al. |
| 2015/0272571 A1 | 10/2015 | Leimbach et al. |
| 2015/0272574 A1 | 10/2015 | Leimbach et al. |
| 2015/0272580 A1 | 10/2015 | Leimbach et al. |
| 2015/0272581 A1 | 10/2015 | Leimbach et al. |
| 2015/0272583 A1 | 10/2015 | Leimbach et al. |
| 2015/0272604 A1 | 10/2015 | Chowaniec et al. |
| 2015/0332609 A1 | 11/2015 | Alexander |
| 2015/0358426 A1 | 12/2015 | Kimball et al. |
| 2015/0371560 A1 | 12/2015 | Lowe |
| 2015/0374378 A1 | 12/2015 | Giordano et al. |
| 2015/0374449 A1 | 12/2015 | Chowaniec et al. |
| 2016/0000437 A1 | 1/2016 | Giordano et al. |
| 2016/0022374 A1 | 1/2016 | Haider et al. |
| 2016/0030240 A1 | 2/2016 | Gonenc et al. |
| 2016/0031091 A1 | 2/2016 | Popovic et al. |
| 2016/0066909 A1 | 3/2016 | Baber et al. |
| 2016/0070436 A1 | 3/2016 | Thomas et al. |
| 2016/0073928 A1 | 3/2016 | Soper et al. |
| 2016/0074103 A1 | 3/2016 | Sartor |
| 2016/0098933 A1 | 4/2016 | Reiley et al. |
| 2016/0104394 A1 | 4/2016 | Miyazaki |
| 2016/0117956 A1 | 4/2016 | Larsson et al. |
| 2016/0133158 A1 | 5/2016 | Sui et al. |
| 2016/0140876 A1 | 5/2016 | Jabbour et al. |
| 2016/0199059 A1 | 7/2016 | Shelton, IV et al. |
| 2016/0220150 A1 | 8/2016 | Sharonov |
| 2016/0220314 A1 | 8/2016 | Huelman et al. |
| 2016/0225288 A1 | 8/2016 | East et al. |
| 2016/0232819 A1 | 8/2016 | Hofstetter et al. |
| 2016/0235494 A1 | 8/2016 | Shelton, IV et al. |
| 2016/0256187 A1 | 9/2016 | Shelton, IV et al. |
| 2016/0256229 A1 | 9/2016 | Morgan et al. |
| 2016/0262736 A1 | 9/2016 | Ross et al. |
| 2016/0262745 A1 | 9/2016 | Morgan et al. |
| 2016/0293055 A1 | 10/2016 | Hofstetter |
| 2016/0296144 A1 | 10/2016 | Gaddam et al. |

FOREIGN PATENT DOCUMENTS

| | | |
|---|---|---|
| CN | 2909427 Y | 6/2007 |
| CN | 101313842 A | 12/2008 |
| CN | 201364679 Y | 12/2009 |
| CN | 201955979 U | 8/2011 |
| CN | 202443680 U | 9/2012 |
| CN | 202563792 U | 11/2012 |
| CN | 202601055 U | 12/2012 |
| CN | 202694651 U | 1/2013 |
| CN | 103050040 A | 4/2013 |
| CN | 203013103 U | 6/2013 |
| CN | 203038549 U | 7/2013 |
| CN | 203338651 U | 12/2013 |
| CN | 203397593 U | 1/2014 |
| CN | 203562128 U | 4/2014 |
| CN | 10388679 A | 6/2014 |
| DE | 41 05 892 A1 | 8/1992 |
| DE | 44 14 832 A1 | 11/1995 |
| EP | 1 024 173 A1 | 8/2000 |
| FR | 2 691 826 A1 | 12/1993 |
| FR | 2 917 876 A1 | 12/2008 |
| GB | 2488994 A | 9/2012 |
| JP | 10 211160 A | 8/1998 |
| JP | 2001005378 A | 1/2001 |
| JP | 2009236963 A | 10/2009 |
| JP | 3162161 U | 8/2010 |
| JP | 2013127496 A | 6/2013 |
| MX | PA 02004422 A | 11/2003 |
| PT | 106230 | 9/2013 |
| WO | WO 1994/06109 A1 | 3/1994 |
| WO | WO 1996/042076 A1 | 2/1996 |
| WO | WO 98/58358 A1 | 12/1998 |
| WO | WO 1999/01074 A1 | 1/1999 |
| WO | WO 2000/36577 A1 | 6/2000 |
| WO | WO 2002/38039 A2 | 5/2002 |
| WO | WO 2002/038039 A3 | 5/2002 |
| WO | WO 2004/032095 A1 | 4/2004 |
| WO | WO 2004/082486 A1 | 9/2004 |
| WO | WO 2005/071639 A1 | 8/2005 |
| WO | WO 2006/083963 A2 | 8/2006 |
| WO | WO 2007/068360 A1 | 6/2007 |
| WO | WO 2008/021720 A2 | 2/2008 |
| WO | WO 2009/000939 A1 | 12/2008 |
| WO | WO 2010/094730 A1 | 8/2010 |
| WO | WO 2011/035410 A1 | 3/2011 |
| WO | WO 2011/046606 A1 | 4/2011 |
| WO | WO 2011/151304 A1 | 12/2011 |
| WO | WO 2012/149606 A1 | 11/2012 |
| WO | WO 2012/168287 A1 | 12/2012 |
| WO | WO 2012/175993 A1 | 12/2012 |
| WO | WO 2013/048978 A1 | 4/2013 |
| WO | WO 2013/103956 A1 | 7/2013 |
| WO | WO 2014/022815 A1 | 2/2014 |
| WO | WO 2014/093669 A1 | 6/2014 |
| WO | WO 2015/148817 A1 | 10/2015 |

OTHER PUBLICATIONS

European Patent Office, International Search Report for International Application No. PCT/US2011/053859 A3, dated Apr. 5, 2012, entitled "Portable Laparoscopic Trainer.".

European Patent Office, The International Search Report and Written Opinion for International Application No. PCT/US2012/60997, dated Mar. 7, 2013, entitled "Simulated Tissue Structure for Surgical Training.".

European Patent Office, The International Search Report and Written Opinion for International Application No. PCT/US2012/070971, dated Mar. 18, 2013, entitled "Advanced Surgical Simulation.".

Human Patient Simulator, Medical Education Technologies, Inc., http://www.meti.com (1999) all.

The International Bureau of WIPO, International Preliminary Report on Patentability and Written Opinion for International Application No. PCT/US2011/053859, titled "Portable Laparoscopic Trainer" dated Apr. 2, 2013.

European Patent Office, The International Search Report and Written Opinion for International Application No. PCT/US2013/061728 dated Oct. 18, 2013, entitled "Surgical Training Model for Laparoscopic Procedures.".

European Patent Office, The International Search Report and Written Opinion for International Application No. PCT/US2013/062363, dated Jan. 22, 2014, entitled "Surgical Training Model for Laparoscopic Procedures.".

European Patent Office, The International Search Report and Written Opinion for International Application No. PCT/US2013/061949, dated Feb. 17, 2014, entitled "Surgical Training Model for Laparoscopic Procedures.".

Anonymous: Realsim Systems—LTS2000, Sep. 4, 2005, pp. 1-2, XP055096193, Retrieved from the Internet: URL:https://web.archive.org/web/2005090403;3030/http://www.realsimsystems.com/exersizes.htm (retrieved on Jan. 14, 2014).

European Patent Office, The International Search Report and Written Opinion for International Application No. PCT/US2013/061557, dated Feb. 10, 2014, entitled "Surgical Training Model for Laparoscopic Procedures.".

European Patent Office, The International Search Report and Written Opinion for International Application No. PCT/US2013/062269, dated Feb. 17, 2014, entitled "Surgical Training Model for Transluminal Procedures.".

(56) References Cited

OTHER PUBLICATIONS

The International Bureau of WIPO, International Preliminary Report on Patentability for International Application No. PCT/US2012/060997, titled "Simulated Tissue Structure for Surgical Training" dated Apr. 22, 2014.
The International Bureau of WIPO, International Preliminary Report on Patentability for International Application No. PCT/US2012/070971 titled "Advanced Surgical Simulation" dated Jun. 24, 2014.
European Patent Office, The International Search Report and Written Opinion for International Application No. PCT/US2014/019840 dated Jul. 4, 2014 entitled "Advanced Surgical Simulation Constructions and Methods.".
European Patent Office, The International Search Report and Written Opinion of the International Searching Authority for International Application No. PCT/US2014/038195 titled "Hernia Model", dated Oct. 15, 2014.
European Patent Office, The International Search Report and Written Opinion of the International Searching Authority for International Application No. PCT/US2014/048027 titled "First Entry Model", dated Oct. 17, 2014.
European Patent Office, The International Search Report and Written Opinion for International Application No. PCT/US2014/042998, title; Gallbladder Model, dated Jan. 7, 2015.
The International Bureau of WIPO, International Preliminary Report on Patentability, for PCT application No. PCT/US2013/053497, titled, Simulated Stapling and Energy Based Ligation for Surgical Training, dated Feb. 12, 2015.
The International Bureau of WIPO, International Preliminary Report on Patentability for International Application No. PCT/US2013/062363, titled Surgical Training Model for Laparoscopic Procedures, dated Apr. 9, 2015.
The International Bureau of WIPO, International Preliminary Report on Patentability for International Application No. PCT/US2013/062269, titled Surgical Training Model for Laparoscopic Procedures, dated Apr. 9, 2015.
The International Bureau of WIPO, International Preliminary Report on Patentability for International Application No. PCT/US2013/061557, titled Surgical Training Model for Laparoscopic Procedures, dated Apr. 9, 2015.
The International Bureau of WIPO, International Preliminary Report on Patentability for International Application No. PCT/US2013/061728, titled Surgical Training Model for Laparoscopic Procedures, dated Apr. 9, 2015.
The International Bureau of WIPO, International Preliminary Report on Patentability for International Application No. PCT/US2013/061949, titled Surgical Training Model for Laparoscopic Procedures, dated Apr. 9, 2015.
European Patent Office, The International Search Report and Written Opinion for International Application No. PCT/US2015/020574, dated Jun. 1, 2015 entitled "Advanced First Entry Model for Surgical Simulation.".
European Patent Office, The International Search Report and Written Opinion for International Application No. PCT/US2015/022774, dated Jun. 11, 2015 entitled "Simulated Dissectible Tissue.".
Anonymous: Silicone rubber-from Wikipedia, the free encyclopedia, pp. 1-6, XP055192375, Retrieved from the Internet: URL:http://en.wikipedia.org/w.index.php?title=Silicone_rubber&oldid=596456058 (retrieved on May 29, 2015).
Lamouche, et al., "Review of tissue simulating phantoms with controllable optical, mechanical and structural properties for use in optical coherence tomography," Biomedical Optics Express, Jun. 1, 2012, 18 pgs., vol. 3, No. 6.
Kurashima Y et al, "A tool for training and evaluation of Laparoscopic inguinal hernia repair; the Global Operative Assessment of Laparoscopic Skills-Groin Hernia" American Journal of Surgery, Paul Hoeber, New York, NY, US vol. 201, No. 1, Jan. 1, 2011, pp. 54-61 XP027558745.
Limps and Things, EP Guildford MATTU Hernia Trainer, http://limbsandthings.com/us/products/tep-guildford-mattu-hernia-trainer/.
Simulab, Hernia Model, http://www.simulab.com/product/surgery/open/hernia-model.
McGill Laparoscopic Inguinal Hernia Simulator, Novel Low-Cost Simulator for Laparoscopic Inguinal Hernia Repair.
University of Wisconsin-Madison Biomedical Engineering, Inguinal Hernia Model, http://bmedesign.engr.wisc.edu/projects/s10/hernia_model/.
The International Bureau of WIPO, International Preliminary Report on Patentability for International Application No. PCT/US2014/019840, titled Simulated Tissue Structure for Surgical Training, dated Sep. 11, 2015.
The International Bureau of WIPO, International Preliminary Report on Patentability for International Application No. PCT/US2014/038195, titled Hernia Model, dated Nov. 26, 2015.
The International Bureau of WIPO, International Preliminary Report on Patentability for International Application No. PCT/US2014/042998, titled "Gallbladder Model" dated Dec. 30, 2015.
European Patent Office, International Search Report and Written Opinion for International Application No. PCT/US2013/053497 titled "Simulated Stapling and Energy Based Ligation for Surgical Training" dated Nov. 5, 2013.
The International Bureau of WIPO, International Preliminary Report on Patentability for International Application No. PCT/US2014/048027, titled "First Entry Model" dated Feb. 4, 2016.
European Patent Office, Invitation to Pay Additional Fees for International Application No. PCT/US2016/062669, titled "Simulated Dissectible Tissue", dated Feb. 10, 2017, 8 pgs.
European Patent Office, The International Search Report and Written Opinion of the International Searching Authority for International Application No. PCT/US2016/055148 titled "Hysterectomy Model", dated Feb. 28, 2017, 12 pgs.
Society of Laparoendoscopic Surgeons, "Future Technology Session: The Edge of Innovation in Surgery, Space, and Business" http://www.laparoscopytoday.com/endourology/page/2/, Figure 1B: http://laparoscopy.blogs.com/laparoscopy_today/images/6-1/6-1VIaovicPicB.jpg , Sep. 5-8, 2007, 10 pgs.
Miyazaki Enterprises, "Miya Model Pelvic Surgery Training Model and Video," www.miyazakienterprises, printed Jul. 1, 2016, 1 pg.
European Patent Office, International Search Report and Written Opinion for International Application No. PCT/US2015/059668 titled "Simulated Tissue Models and Methods" dated Apr. 26, 2016, 20 pgs.
Australian Patent Office, Patent Examination Report No. 1 for Australian Application No. 2012358851 titled "Advanced Surgical Simulation" dated May 26, 2016, 3 pgs.
European Patent Office, International Search Report and Written Opinion for International Application No. PCT/US2016/032292 titled "Synthetic Tissue Structures for Electrosurgical Training and Simulation," dated Jul. 14, 2016, 11 pgs.
European Patent Office, International Search Report and Written Opinion for International Application No. PCT/US2016/018697 titled "Simulated Tissue Structures and Methods," dated Jul. 14, 2016, 21 pgs.
European Patent Office, International Search Report and Written Opinion for International Application No. PCT/US2016/034591 titled "Surgical Training Model for Laparoscopic Procedures," dated Aug. 8, 2016, 18 pgs.
European Patent Office, The International Search Report and Written Opinion of the International Searching Authority for International Application No. PCT/US2016/036664 titled "Hysterectomy Model", dated Aug. 19, 2016, 15 pgs.
The International Bureau of WIPO, International Preliminary Report on Patentability for International Application No. PCT/US2015/020574, entitled "Advanced First Entry Model for Surgical Simulation," dated Sep. 22, 2016, 9 pgs.
European Patent Office, The International Search Report and Written Opinion of the International Searching Authority for International Application No. PCT/US2016/0043277 titled "Appendectomy Model", dated Oct. 4, 2016, 12 pgs.

(56) References Cited

OTHER PUBLICATIONS

The International Bureau of WIPO, International Preliminary Report on Patentability for International Application No. PCT/US2015/022774, titled "Simulated Dissectible Tissue," dated Oct. 6, 2016, 9 pgs.
European Patent Office, The International Search Report and Written Opinion of the International Searching Authority for International Application No. PCT/US2016/041852 titled "Simulated Dissectible Tissue", dated Oct. 13, 2016, 12 pgs.
3D-MED Corporation, "Validated Training Course for Laparoscopic Skills", https://www.3-dmed.com/sites/default/files/product-additional/product-spec/Validated%20Training%20Course%20for%20Laparoscopic%20Skills.docx_3.pdf, printed Aug. 23, 2016, pp. 1-6.
3D-MED Corporation, "Loops and Wire #1" https://www.3-dmed.com/product/loops-and-wire-1 , printed Aug. 23, 2016, 4 pgs.
Barrier, et al., "A Novel and Inexpensive Vaginal Hysterectomy Simulatory," Simulation in Healthcare: The Journal of the Society for Simulation in Healthcare, vol. 7, No. 6, Dec. 1, 2012, pp. 374-379.
European Patent Office, Examination Report for European Application No. 14733949.3 titled "Gallbladder Model," dated Dec. 21, 2016, 6 pgs.
European Patent Office, The International Search Report and Written Opinion of the International Searching Authority for International Application No. PCT/US2016/062669 titled "Simulated Dissectible Tissue," dated Apr. 5, 2017, 19 pgs.
European Patent Office, The International Search Report and Written Opinion of the International Searching Authority for International Application No. PCT/US2017/020389 titled "Simulated Tissue Cartridge", dated May 24, 2017, 13 pgs.
The International Bureau of WIPO, International Preliminary Report on Patentability and Written Opinion for International Application No. PCT/US2015/059668, entitled "Simulated Tissue Models and Methods," dated May 26, 2017, 16 pgs.
The International Bureau of WIPO, International Preliminary Report on Patentability for International Application No. PCT/US2016/018697, entitled "Simulated Tissue Structures and Methods," dated Aug. 31, 2017, 14 pgs.
The International Bureau of WIPO, International Preliminary Report on Patentability for International Application No. PCT/US2016/0032292, entitled "Synthetic Tissue Structures for Electrosurgical Training and Simulation," dated Nov. 23, 2017, 2017, 8 pgs.
The International Bureau of WIPO, International Preliminary Report on Patentability for International Application No. PCT/US2016/034591, entitled "Surgical Training Model for Laparoscopic Procedures," dated Dec. 7, 2017, 2017, 14 pgs.
The International Bureau of WIPO, International Preliminary Report on Patentability for International Application No. PCT/US2016/041852, entitled "Simulated Dissectible Tissue," dated Jan. 25, 2018, 12 pgs.
European Patent Office, Extended European Search Report for European Patent Application No. EP 17202365.7, titled "Gallbladder Model", dated Jan. 31, 2018, 8 pgs.
The International Bureau of WIPO, International Preliminary Report on Patentability for International Application No. PCT/US2016/043277, entitled "Appendectomy Model," dated Feb. 1, 2018, 9 pgs.
The International Bureau of WIPO, International Preliminary Report on Patentability for International Application No. PCT/US2016/036664, entitled "Hysterectomy Model," dated Dec. 21, 2017, 10 pgs.
The International Bureau of WIPO, International Preliminary Report on Patentability for International Application No. PCT/US2016/055148, entitled "Hysterectomy Model," dated Apr. 12, 2018, 12 pgs.

\* cited by examiner

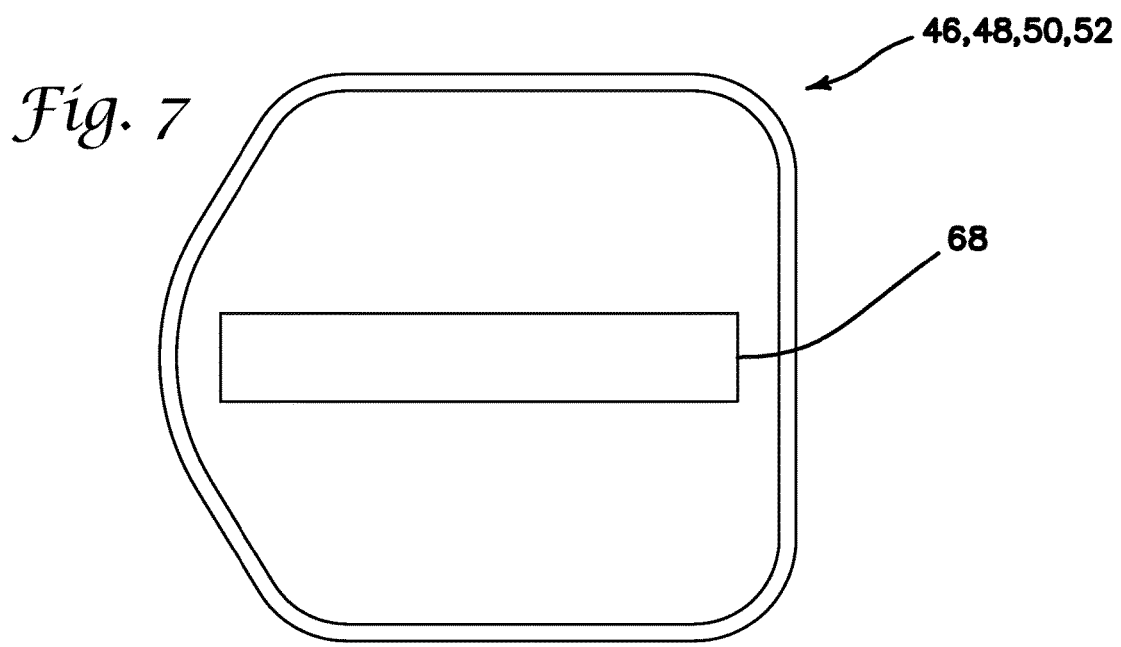
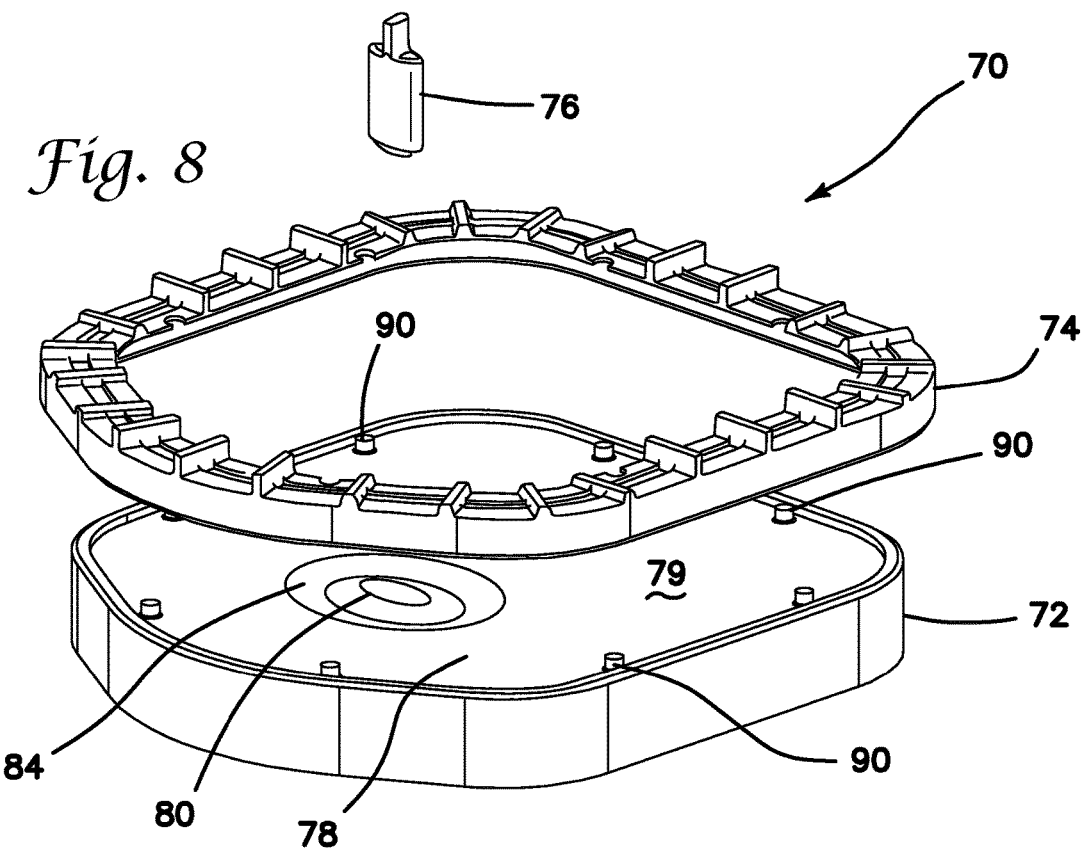

ADVANCED FIRST ENTRY MODEL FOR SURGICAL SIMULATION

CROSS-REFERENCE TO RELATED APPLICATIONS

This application claims priority to and benefit of U.S. Provisional Patent Application Ser. No. 61/952,289 entitled "Advanced first entry model for surgical simulation" filed on Mar. 13, 2014; this application also claims priority to and benefit of U.S. Provisional Patent Application Ser. No. 61/971,714 entitled "First entry model" filed on Mar. 28, 2014; and this application is a continuation-in-part of U.S. patent application Ser. No. 14/340,234 entitled "First entry model" filed on Jul. 24, 2014 which claims benefit and priority to U.S. Provisional Patent Application Ser. No. 61/857,982 entitled "First entry model" filed on Jul. 24, 2013, all of which are incorporated herein by reference in their entireties.

FIELD OF THE INVENTION

This application relates to surgical training tools, and in particular, to simulated tissue structures and models for teaching and practicing surgical procedures.

BACKGROUND OF THE INVENTION

Laparoscopic surgery requires several small incisions in the abdomen for the insertion of trocars or small cylindrical tubes approximately 5 to 10 millimeters in diameter through which surgical instruments and a laparoscope are placed into the abdominal cavity. The laparoscope illuminates the surgical field and sends a magnified image from inside the body to a video monitor giving the surgeon a close-up view of organs and tissues. The surgeon watches the live video feed and performs the operation by manipulating the surgical instruments placed through the trocars.

The first step in laparoscopic surgery is to make a small incision to access the abdomen and create pneumoperitoneum. Pneumoperitoneum is the insufflation of the abdominal cavity with carbon dioxide gas. Insufflation with gas creates a working space in the abdomen necessary for laparoscopy. Once a proper working space has been created, surgical instruments can be inserted for performing a laparoscopic procedure. This process of penetrating the abdomen and creating pneumoperitoneum prior to insertion of other instruments is called first entry. There are many different ways to achieve pneumoperitoneum. One option is using a Veress needle. A Veress needle is approximately 12-15 centimeters long with a diameter of approximately 2 millimeters. The surgeon inserts the spring-loaded needle into the abdomen of the patient after making a small incision. When the needle breaches the inner abdominal space, the spring-loaded inner stylet springs forward to cover the sharp needle in order protect internal organs. The surgeon relies on the feel and sound of the needle and spring for proper placement. Once proper entry is confirmed, carbon dioxide is introduced through the Veress needle and into the abdominal cavity of the patient expanding the abdomen to creating a working space.

Another option is a Hasson technique or cut down technique in which the surgeon makes an initial incision at the umbilicus and the tissue is bluntly dissected. A suture is placed on either side of the incision into the fascia layer to help hold the device in place. The supraperitoneal tissue is dissected away and the peritoneum is incised to enter the abdominal cavity. At this point, a Hasson trocar is inserted into the incision. The Hasson trocar has a blunt tip with suture ties and/or a balloon to hold it in place. After the trocar is placed into the incision, the device is secured with sutures and/or the balloon and carbon dioxide gas is pumped into the patient through the trocar to achieve pneumoperitoneum.

Another option is direct trocar entry. In this option, the surgeon uses a bladed or non-bladed trocar. The trocar can be used optically in which a specialized trocar is configured to receive a laparoscope and a laparoscope is inserted into the trocar before entry in order to view the penetration as it occurs. Also, the trocar may be use non-optically without a laparoscope inside. After the initial incision is made, the trocar is placed through the layers of the abdomen. Since the camera is present, all of the layers of the abdominal wall can be observed during penetration. Once the surgeon sees that he or she has broken through the peritoneum, penetration can halt, the obturator tip of the trocar pulled back slightly or removed entirely and insufflation can commence by pumping carbon dioxide gas in through the cannula to create pneumoperitoneum.

Another option involves a specialized first entry trocar such as the FIOS® first entry trocar made by Applied Medical Resources Corporation in California. Like optical direct trocar entry, a laparoscope is inserted into the FIOS® trocar and the abdominal wall layers are observed during insertion into the abdominal cavity. The specialized FIOS® trocar has a small vent hole in the tip such that instead of requiring that the obturator of the trocar be pulled back or removed completely to introduce carbon dioxide through the cannula, carbon dioxide gas is introduced through the small vent hole in the tip of the obturator with the camera in place. Because carbon dioxide can be introduced through the tip, the FIOS® trocar does not have to penetrate as deeply into the abdominal cavity as a traditional trocar, thereby, affording internal organs greater protection before insufflation can commence. Also, because the obturator does not have to be pulled back or removed, observation via the inserted camera can take place at the point of insufflation.

In addition to the above options for entering the abdominal cavity, generally, there are two common places on the abdomen that a surgeon must know how to enter. The most widely used location for first entry is the umbilicus. The umbilicus is a natural weakening in the abdomen where the umbilical cord was attached in the womb. In this part of the abdomen, there are no rectus muscles, arteries or veins so it is generally easier to reach the abdominal cavity. Additionally, the umbilicus is typically an easy place to hide a scar. When surgeons use the umbilicus as an entry site, particularly for the Hasson technique, clamps are often used to grab the base of the umbilicus and the umbilicus is inverted. At this point, an incision is made and the surgeon cuts down as desired and inserts the trocar or Veress needle. With optical entry, the surgeon is able to see all the layers of the abdominal wall. In this location of penetration, they are able to see the fatty tissue, linea *alba, transversalis* fascia and, finally, the peritoneum. Additionally, when entering at the umbilicus, the umbilical stalk should also be visible. The stalk is what remains of the umbilical cord and it stretches from the skin making up the umbilicus to the peritoneal layer.

If a patient has had a previous surgery and adhesions are suspected or a hernia is present at the site of the umbilicus, first entry may need to occur at another location. In this case, the surgeon will often enter from the left upper quadrant since there is less chance of damaging a vital organ in this location. The left upper quadrant is different from the umbilicus region in that there are muscle layers. The rectus abdominus muscles run parallel with the patient's abdomen and are found on either side of the patient's midline. Underneath the rectus abdominus muscles run the inferior epigastric veins and arteries which the surgeon must be careful to avoid. When a surgeon is entering the upper quadrant of the abdominal cavity optically, he or she is able to see the skin, fatty tissue, anterior rectus sheath, rectus abdominus, the epigastric vein, which runs through the posterior rectus sheath, and finally, the peritoneum. If the left upper quadrant is not an ideal position for a port, the surgeon may choose to enter at another location such as sub-xiphoid where subcutaneous fat, rectus sheath and peritoneum are present.

Since there are many options for first entry, it is important that surgeons have a way to learn and practice the various techniques. There is a need for an anatomical model of the umbilical region and surrounding abdomen that is anatomically correct and includes all the layers of the abdominal wall as well as the veins and arteries that run through the wall. Not only does the model have to be anatomically correct, but also, the model must provide a realistic aural and tactile sensation. For example, when using a Veress needle, two pops are generally felt as the surgeon pushes the needle through the abdominal wall. For optical entry, the surgeon needs to view all of the appropriate tissue layers in the abdominal wall. For entry through the umbilicus, the surgeon must be able to grasp and invert the umbilicus. Also, the model may be able to be used with all four first entry techniques and at multiple (umbilical and upper left quadrant at minimum) entry sites.

SUMMARY OF THE INVENTION

According to one aspect of the invention, a surgical training device is provided. The training device includes a simulated tissue structure having an upper surface and a lower surface. The tissue structure includes at least one layer that simulates a tissue layer such as that of an abdominal wall. The training device includes a receptacle connected to the lower surface of the simulated tissue structure. The receptacle has a wall that defines an interior and exterior of the receptacle. The training device further includes one or more simulated organs or simulated tissue structures located in the interior of the receptacle. The simulated organs are configured to be located proximally to the simulated tissue structure and when one or more of the simulated tissue structure and receptacle are penetrated by a surgical instrument such as an optical trocar at least part of the one or more simulated organs or simulated tissue structures inside the receptacle translate distally away from the simulated tissue structure to simulate surgical insufflation of an abdominal cavity.

According to another aspect of the invention, a surgical training device is provided. The surgical training device includes a penetrable simulated tissue structure configured to simulate an abdominal wall. As such, the penetrable simulated tissue structure may include a plurality of layers. The training device includes a receptacle connected to the tissue structure. The receptacle has a wall defining an interior and an exterior to the receptacle. The receptacle also has a first configuration and a second configuration. The training device further includes at least one tissue simulation located inside the receptacle. While in the first configuration of the receptacle, the tissue simulation inside the receptacle is located proximally to the simulated tissue structure relative to the second configuration wherein while in the second configuration at least part of the tissue simulation inside the receptacle is located distally from simulated tissue structure relative to the first configuration. The training device is configured such that fluid is transferable into the receptacle to convert the receptacle from a first configuration to a second configuration.

According to another aspect of the invention, a surgical training device for training laparoscopic first entry surgical techniques is provided. The training device includes a simulated abdominal wall that is penetrable with an optical trocar. The surgical training device further includes a receptacle containing a tissue simulation located inside the receptacle. The tissue simulation is observable via scope placed inside the optical trocar. Upon penetration of the one or more of the simulated abdominal wall and receptacle, the training device is configured such that the tissue simulation appears to translate away from distally relative to the simulated abdominal wall. The distal translation is effected by the release of negative pressure inside the receptacle upon penetration or as a result of penetration. The distal translation is also effected by the expansion of an elastic wall of the receptacle with the introduction of fluid under pressure into the receptacle upon penetration or as a result of the penetration.

According to another aspect of the invention, a method for simulating surgical insufflation is provided. The method includes the step of providing a model comprising a penetrable artificial tissue structure configured to simulate an abdominal wall. The model includes a receptacle having a wall connected to the artificial tissue structure. The model includes at least one tissue simulation disposed inside the receptacle and located proximally to the artificial tissue structure. The method includes the step of moving a distal tip of an optical surgical obturator through the artificial tissue structure and into the receptacle. The method includes the step of observing the tissue simulation inside the receptacle through the distal end of the optical obturator. The method includes the step of moving the tissue simulation from a position proximal to the artificial tissue structure to a position relatively distal to the artificial tissue structure to simulate insufflation of an abdominal cavity. The method may further including the step creating a vacuum inside the receptacle and wherein the step of moving the tissue simulation includes breaking the vacuum inside the receptacle. The method may further include the step of providing a receptacle with an elastic wall. The method may further include the step of transferring fluid into the receptacle and wherein the step of moving the tissue simulation includes expanding the elastic wall of the receptacle. The method may further include the steps of providing a laparoscopic trainer having a cavity and a floor for the cavity and suspending the model above the floor of the cavity inside the laparoscopic trainer.

According to another aspect of the invention, a model that allows users to practice first entry surgical procedures is provided. The first entry model includes an anatomical portion connected to a support. The anatomical portion includes a plurality of anatomical layers that is captured between two frame elements which can attach to a laparoscopic trainer or as a sales demonstration device.

BRIEF DESCRIPTION OF THE DRAWINGS

FIG. 7 is a top planar view that is representative of more than one layer in an anatomical portion of a first entry model according to the present invention.

FIG. 8 is top perspective, exploded view of a mold for a skin layer of a first entry model according to the present invention.

DETAILED DESCRIPTION OF THE INVENTION

Figure 1:
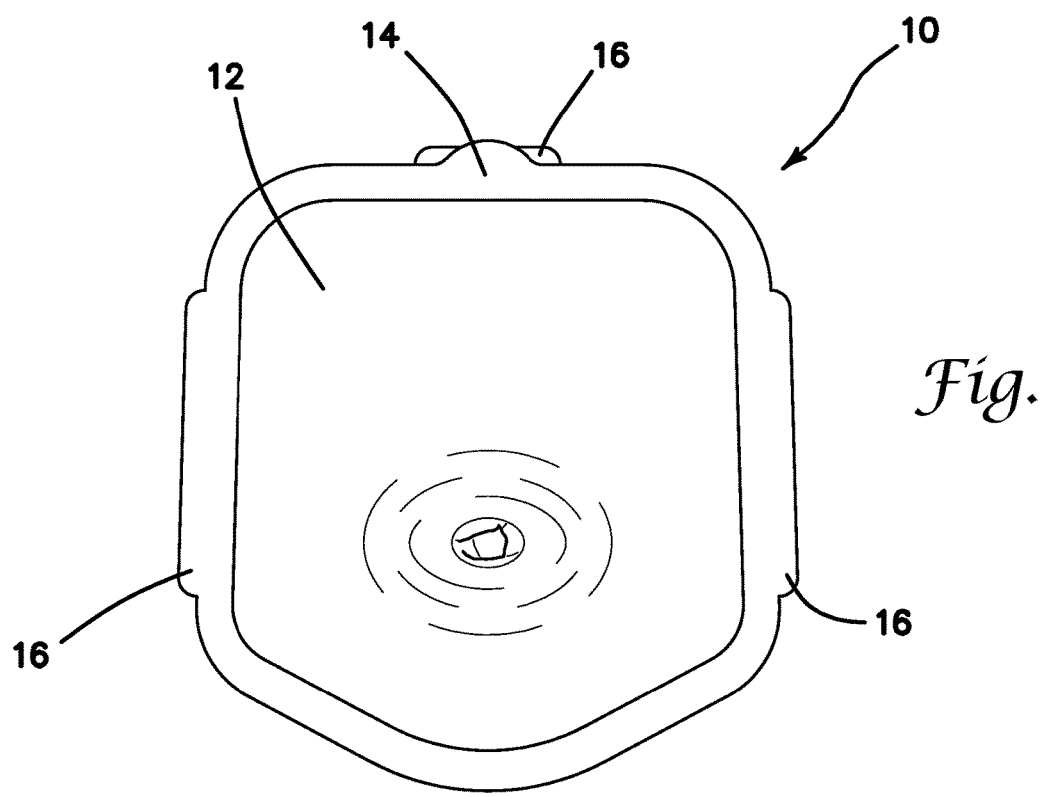
FIG. 1 is a top perspective view of a first entry model according to the present invention.
Figure 2:
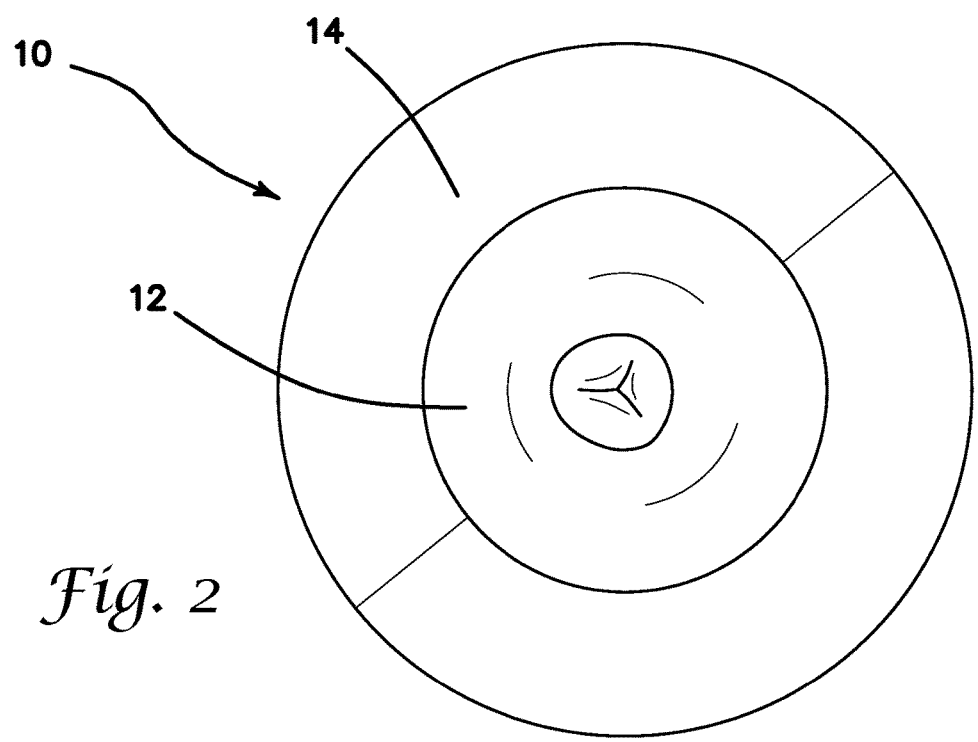
FIG. 2 is top perspective view of a first entry model according to the present invention.

Turning now to FIG. 1, there is shown a model 10 of an abdominal region that includes the umbilicus for practicing surgical first entry into the abdominal cavity for performing laparoscopic surgical procedures. Throughout this specification the model 10 will be referred to as the first entry model 10. The model 10 includes an anatomical portion 12 connected to a support 14 to form a substantially planar configuration. The support 14 is a frame that encompasses and connects to the perimeter of the anatomical portion 12 and holds the anatomical portion 12 together. In particular, the support 14 includes a top frame and a bottom frame made of plastic material sufficiently rigid to provide structural support and maintain the planar shape of the model 10 and permit the center-located anatomical portion to be penetrated from one side to the other. In one variation, the model 10 is slightly curved to mimic an outwardly curved abdomen. The top frame and the bottom frame snap together capturing the perimeter of the anatomical portion 12 between the top and bottom frames. The model 10 in FIG. 1 is polygonal having five sides forming a slightly elongated shape wherein one side is curved outwardly in a generally U-shaped configuration. A model 10 having a circular support 14 that frames a circular anatomical portion 12 is shown in FIG. 2. The model 10 can be any shape. The frame 14 includes connecting elements 16 configured for connecting the model 10 to a larger laparoscopic trainer as shown in FIG. 3.

Figure 3:
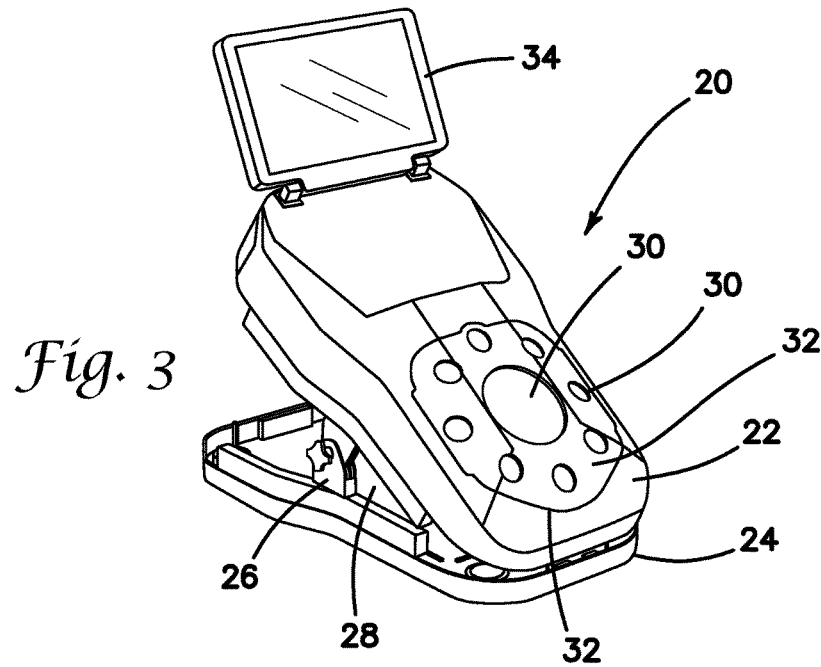
FIG. 3 is a top perspective view of a laparoscopic trainer for use with a first entry model according to the present invention.

Turning now to FIG. 3, a laparoscopic trainer 20 includes a top cover 22 connected to a base 24 by a pair of legs 26 spacing the top cover 22 from the base 24. The laparoscopic trainer 20 is configured to mimic the torso of a patient such as the abdominal region. The top cover 22 is representative of the anterior surface of the patient and a space 28 defined between the top cover 22 and the base 24 is representative of an interior of the patient or body cavity where organs reside. The laparoscopic trainer 20 is a useful tool for teaching, practicing and demonstrating various surgical procedures and their related instruments in simulation of a patient. When assembled, the top cover 22 is positioned directly above the base 24 with the legs 26 located substantially at the periphery and interconnected between the top cover 22 and base 24. The top cover 22 and base 24 are substantially the same shape and size and have substantially the same peripheral outline. The laparoscopic trainer 20 includes a top cover 22 that angulates with respect to the base 24. The legs 26 are configured to permit the angle of the top cover 22 with respect to the base 24 to be adjusted. FIG. 3 illustrates the trainer 20 adjusted to an angulation of approximately 30-45 degrees with respect to the base 24. A laparoscopic trainer 20 is described in co-pending U.S. patent application Ser. No. 13/248,449 entitled "Portable laparoscopic trainer" and filed on Sep. 29, 2011 by Pravong et al. to Applied Medical Resources Corporation and published as U.S. Patent Application Publication No. 2012/0082970, hereby incorporated by reference in its entirety herein.

For practicing various surgical techniques, surgical instruments are inserted into the cavity 28 of the laparoscopic trainer 20 through pre-established apertures 30 in the top cover 22. These pre-established apertures 30 may include seals that simulate trocars or may include simulated tissue that simulates the patient's skin and abdominal wall portions. For example, the circular first entry model 10 depicted in FIG. 2 is connected to the top cover 22 in the location of the central circular aperture 30 that has a conforming circular shape. The top cover 22 of the laparoscopic trainer 20 is configured with a removable insert 32 that is replaceable with the first entry model 10 depicted in FIG. 1. The insert 32 which is provided with apertures 30 has a shape that conforms to an opening in the top cover 22. When the insert 32 is removed, the first entry model 10, such as the one depicted in FIG. 1, having a conforming shape is inserted into the opening in the top cover 20 and the connecting elements 16 on the first entry model 10 aid in securing the model 10 to the trainer 20.

Various tools and techniques may be used to penetrate the top cover 20 as described in the background of this description to perform mock procedures not only on the model 10 but also on additional model organs placed between the top cover 22 and the base 24. When placed inside the cavity 28 of the trainer 20, an organ model is generally obscured from the perspective of the user who can then practice performing surgical techniques laparoscopically by viewing the surgical site indirectly via a video feed displayed on a video monitor 34. The video display monitor 34 is hinged to the top cover 22 and is shown in an open orientation in FIG. 3. The video monitor 34 is connectable to a variety of visual systems for delivering an image to the monitor 34. For example, a laparoscope inserted through one of the pre-established apertures 30 or a webcam located in the cavity 28 and used to observe the simulated procedure can be connected to the video monitor 34 and/or a mobile computing device to provide an image to the user. After first entry procedures are practiced on a first entry model 10 connected to the trainer 20, the first entry model 10 is removed and may be replaced with a new insert or reconstructed and reconnected to the trainer 20 to allow training to continue or be repeated. Of course, the first entry model 10 may be employed independently of the trainer 20 for practicing first entry techniques.

Figure 4:
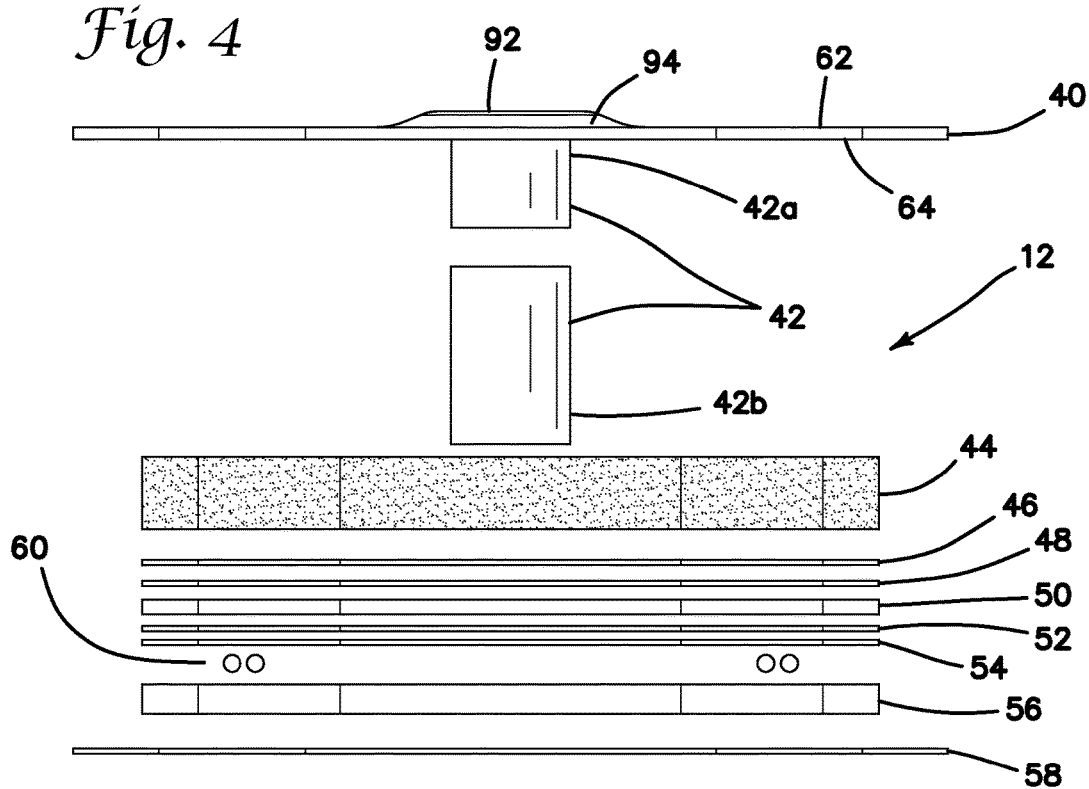
FIG. 4 is a side, exploded view of an anatomical portion of a first entry model according to the present invention.
Figure 5:
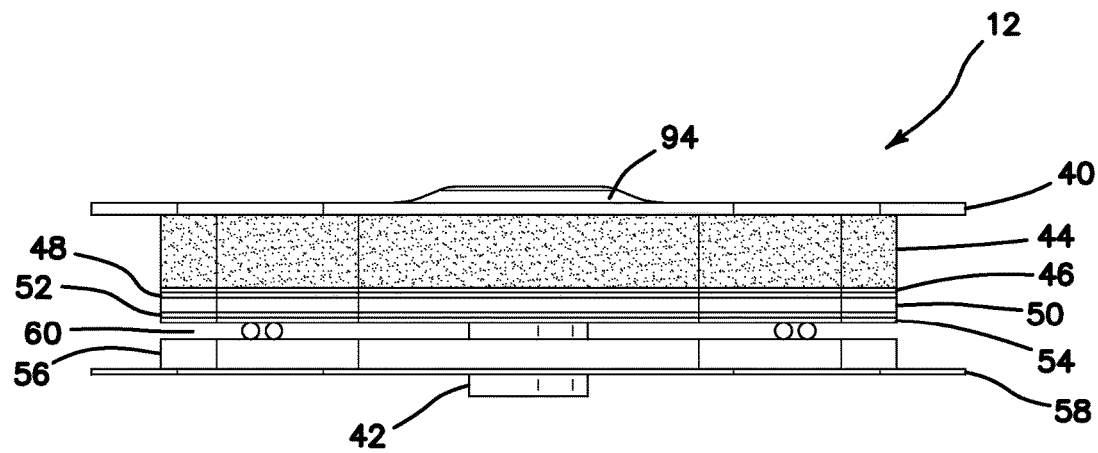
FIG. 5 is a side view of an anatomical portion of a first entry model according to the present invention.
Figure 6:
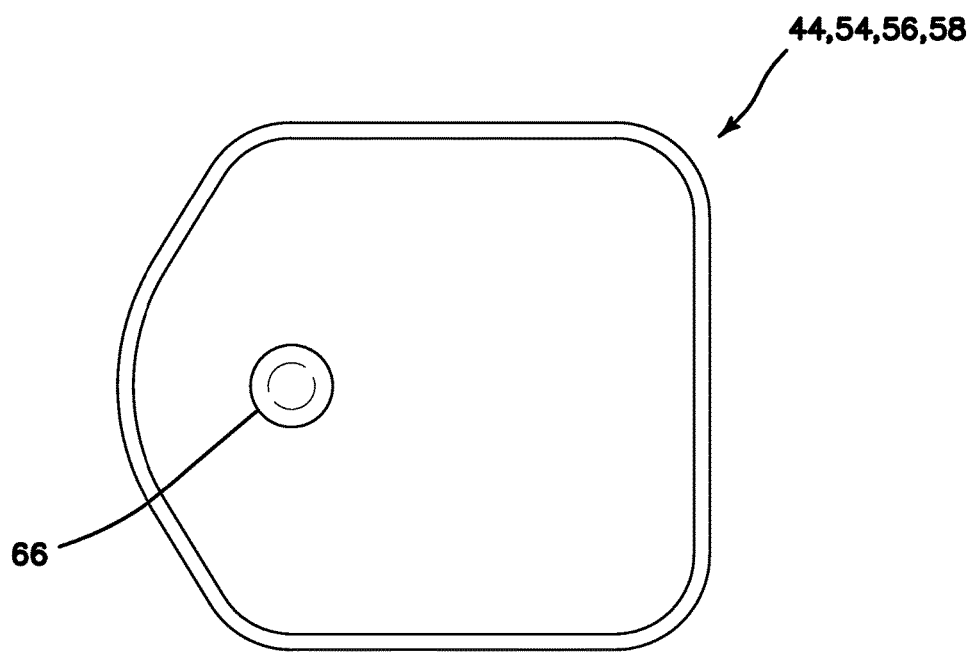
FIG. 6 is a top planar view that is representative of more than one layer in an anatomical portion of a first entry model according to the present invention.

Turning now to FIGS. 4 and 5, the anatomical portion 12 of the first entry model 10 will now be described. The anatomical portion 12 includes a skin layer 40, an umbilical stalk 42, a fat layer 44, an anterior rectus sheath layer 46, a first rectus muscle layer 48, a second rectus muscle layer 50, a third rectus muscle layer 52, a posterior rectus sheath layer 54, a transversalis fascia layer 56, and a peritoneum layer 58. The layers 40, 44, 46, 48, 50, 52, 54, 56, 58 are placed one on top of the other as shown in FIGS. 5-6 with the umbilical stalk 42 penetrating through all of the layers beneath the skin layer 40. The layers 40, 44, 46, 48, 50, 52, 54, 56, 58 are connected together with adhesive or other fastener. In one variation, the layers 40, 44, 46, 48, 50, 52, 54, 56 are connected with at least one price-tag holder punched through the layers and sandwiched between the skin layer 40 and the peritoneum layer 58 before being attached to the frame 14. In another variation, the layers are held together without adhesive or other fastener and clamped between the top frame and bottom frame. An optional inferior epigastric vein and artery layer 60 is included between the posterior rectus sheath layer 54 and the transversalis fascia layer 56 as shown in FIGS. 4-5.

With continued reference to FIG. 4, the skin layer 40 is molded of silicone or thermoplastic elastomer dyed with a flesh color. The skin layer 40 includes a top surface 62 and bottom surface 64 defining a thickness of approximately 0.1 inches. The skin layer 40 includes an integrally formed umbilical stalk portion 42a. The skin layer 40 will be described in greater detail below.

Still referencing FIG. 4, the fat layer 44 is made of cellular polyethylene foam having a yellow color. The cellular foam layer is not solid but textured with air bubbles. The fat layer 44 is approximately 0.625 inches thick. The anterior rectus sheath layer 46 is made of solid ethylene vinyl acetate (EVA) foam having a white color and is approximately 1 millimeter thick. The first rectus muscle layer 48 is made of solid EVA foam and is red in color and approximately 1 millimeter thick. The second rectus muscle layer 50 is made of cellular polyethylene foam having a pink color. The second rectus muscle layer 50 is cellular foam that includes air bubbles that provide a cellular texture and is approximately 0.125 inches thick. The third rectus muscle layer 52 is made of solid EVA foam having a red color and is approximately 1 millimeter thick. The posterior rectus sheath layer 54 is made of solid EVA foam that is white in color and is approximately 1 millimeter thick. The transversalis fascia layer 56 is made of cellular polyethylene foam that is white in color and approximately 0.25 inches thick. The fascia layer 56 has a cellular texture arising from the cellular polyethylene foam as opposed to the solid EVA foam layers. The peritoneum layer 58 is made of solid EVA foam that is white in color and approximately 1 millimeter thick. The inferior epigastric vein and artery layer 60 include solid or hollow elongate cylindrical structures made of silicone or Kraton polymer or other elastomer having a cross-sectional diameter of approximately 0.15 inches. The arteries are red in color and the veins are blue in color. The layers as described above provide an optical entry with a very realistic appearance to the end user.

Turning now to FIG. 6, there is shown a top planar view that is representative of the fat layer 44, the posterior rectus sheath layer 54, the transversalis fascia layer 56 and the peritoneum layer 58. These layers are approximately six inches wide and six and a half inches long. The fat layer 44, the posterior rectus sheath layer 54, the transversalis fascia layer 56 and the peritoneum layer 58 all have a circular aperture 66 that is approximately one inch in diameter. The aperture 66 is located approximately two inches from one side and is in the same place in all of these layers 44, 54, 56, 58 such that when overlaid the apertures 66 line up to provide a pathway for the umbilical stalk 42 across these layers.

Turning now to FIG. 7, there is shown a top planar view that is representative of the anterior rectus sheath layer 46, first rectus muscle layer 48, the second rectus muscle layer 50 and the third rectus muscle layer 52. These layers are approximately six inches wide and six and a half inches long. The anterior rectus sheath layer 46, first rectus muscle layer 48, the second rectus muscle layer 50 and the third rectus muscle layer 52 all have an elongate opening 68. The elongate opening 68 extends along the center line of the layers and is shown in FIG. 7 to be a rectangular cut out that is approximately one inch wide and 5.75 inches long. When the layers 46, 48, 50, 52 are overlaid, one on top of the other, all of the respective openings 68 are aligned. When the layers 46, 48, 50, 52 are overlaid with the other layers 44, 54, 56, 58, the apertures 66 are in communication or alignment with the elongate openings 68. The elongate opening 68 represents the linea alba of the abdomen.

Figure 9:
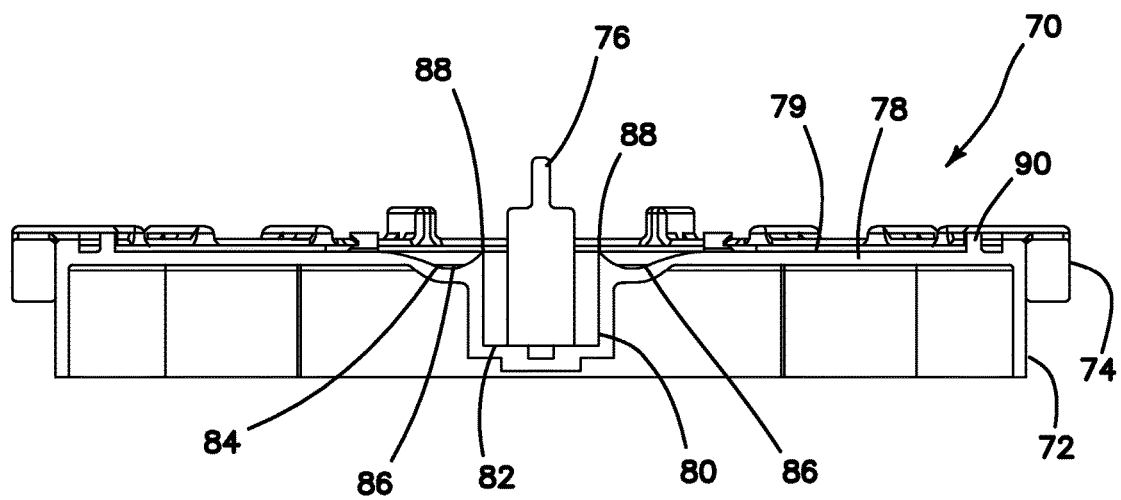
FIG. 9 is a side, cross-sectional view of a mold for a skin layer for a first entry model according to the present invention.
Figure 10:
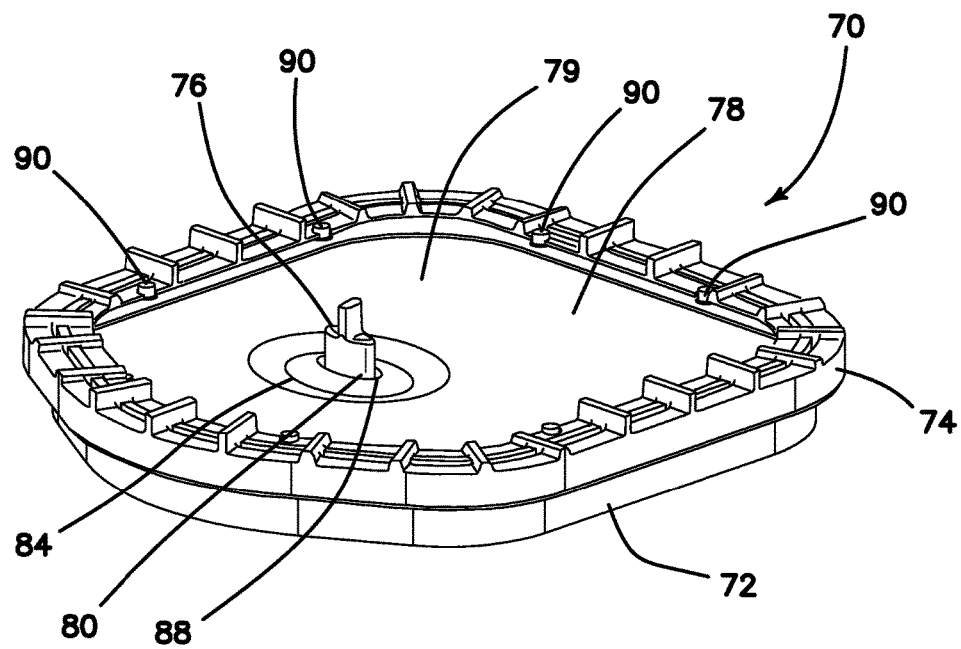
FIG. 10 is a top perspective view of a mold for a skin layer for a first entry model according to the present invention.

With reference back to FIG. 4 and additional reference to FIGS. 8-10, the skin layer 40 is formed by pouring the uncured and dyed silicone or thermoplastic elastomer into a special mold 70. An exploded, top perspective view of the mold 70 is shown in FIG. 8. The mold 70 includes a base 72, a top 74, and a core 76. The base 72 of the mold 70 includes a cavity 78 for receiving the plastic material. The cavity 78 is polygonal and substantially rectangular in shape. The cavity 78 includes a first floor 79 that surrounds a well 80 having a second floor 82. The second floor 82 of the well 80 is approximately 1 inch below the first floor 79 and includes a hole for inserting the core 76 inside the well 80. The cross-section of the well 80 is elliptical in shape having a long axis of approximately 1 inch and a short axis of approximately half an inch. The cross-section of the core 76 is also elliptical in shape, complementary to the well 80. The core 76 has a long axis of approximately 0.75 inches and a short axis of approximately 0.25 inches. With the core 76 in place inside the well 80 a space of approximately ⅛ inch is formed all around the core 76 between the outer surface of the core 76 and the inner surface of the well 80 into which silicone or thermoplastic elastomer is poured to form a tubular structure of the umbilical stalk 42a having an opening 92. The core 76 is approximately one inch and a half in length and extends above the pour line when inside the well 80.

The mold cavity 78 further includes a circumferential well 84 that is formed circumferentially around the first well 80. The circumferential well 84 has a concave or curved floor 86 that is approximately ⅛ inch deeper from the first floor 79. When silicone or thermoplastic elastomer is poured, an elliptical toroidal shape with a flat top is formed in the plastic material resulting in an increased thickness of material of approximately 0.25 inch in the area of the circumferential well 84 in the final product. The circumferential well 84 has an inner perimeter 88 that coincides with the wall of the first well 80. The annular distance from the inner perimeter 88 of the circumferential well 84 to the outer perimeter or end of circumferential well 84 is approximately 0.75 inches. The base 72 of the mold 70 further includes a plurality of pegs 90 upstanding from the first floor 79 to form holes in the resulting molded material. Although the first well 80 is described to have an elliptical shape, in another variation it is circular in shape with a corresponding circular core and circular circumferential well.

The core 76 is first inserted into the well 80 and silicone or thermoplastic elastomer is poured into the base 72 of the mold 70. The silicone or thermoplastic elastomer will run into the well 80 forming a tubular structure defined by the space between the core 76 and wall of the well 80. The silicone or thermoplastic elastomer will also run into the circumferential well 84 and cover the concave floor 86 forming a substantially toroidal shape of increased thickness of approximately 0.25 inch. The circumferential portion of increased thickness 94 is visible in FIGS. 4 and 5. The silicone or thermoplastic elastomer in its liquid state will cover the first floor 79 forming a planar area having a thickness of approximately ⅛ inch. The top 74 of the mold 70 will be placed over the base 72 of the mold 70. The top 74 is configured to cover only the perimeter of the poured silicone or thermoplastic elastomer to reduce the thickness of the silicone around the perimeter.

After the silicone or thermoplastic elastomer has solidified, the top 74 of the mold is removed and the molded silicone or thermoplastic elastomer is removed from the mold 70. The core 76 is also removed from the material leaving an elliptical opening 92 through the skin layer 40. The tubular structure or umbilical stalk 42a that is integrally formed by the well 80 with the rest of the skin layer 40 defines an opening 92 and is elliptical in shape having long axis of approximately 0.75 inches and a short axis of approximately 0.25 inches with a wall thickness of approximately ⅛ inch. The tubular structure 42a is inverted, that is, it is pushed through the opening 92 such that the surface in contact with the floor 79 of the mold 70 becomes the skin layer top surface 62. This advantageously permits the floor 79 of the mold to include texturing that would impart skin-like texture to the skin layer top surface 62. Also, by inverting the tubular structure 42a, not only an umbilical stalk is formed, but also, the portion of increased thickness 94 of the skin layer 40 will advantageously create a raised surface at the skin layer top surface 62 which is clearly visible in FIGS. 4 and 5. This raised portion 94 advantageously provides extra thickness of material for drawing sutures through and maintaining them in position without pulling through the silicone or thermoplastic material. Also, a circumferential raised portion 94 that surrounds the opening 92 creates a realistic belly-button effect that can be seen in FIG. 1. A variation of the skin layer 40 without the raised circumferential portion 94 is shown in FIG. 2. Although the umbilical stalk is approximately one inch long, it may be molded to be longer, approximately 1.25 inches to approximately 2.0 inches long. The skin layer 40 is planar sheet of molded material having a top surface 62 and a bottom surface 64 defining a skin layer thickness of approximately 0.1 inches. The skin layer 40 further includes an opening 92 with a tubular extension 42 integrally formed at opening 92 and interconnected with the rest of the layer 40. Surrounding the opening 92 is a circumferential raised portion 94 of increased thickness of approximately 0.2 inches. The raised portion 94 provides a convex outer surface that transitions into the remainder of the top surface 62 of the skin layer 40.

The mold 70 is 3D printed from Vero White Plus Fullcure 835 material. The distance from the pour line to the floor 79 is approximately 0.1 inches to create a skin layer thickness of approximately 0.1 inches. Around the perimeter, the thickness beneath the top 74 of the mold 70 is reduced to approximately 0.05 inches for a resulting skin layer thickness at the perimeter having a reduced thickness of approximately 0.05 inches which facilitates connection to the frame support 14. At the circumferential well 84 location, the thickness of the resulting skin layer 40 is approximately 0.2 inches. First, the mold 70 is sprayed with mold release solution and allowed to dry. In one variation, approximately 5 grams of Dragon Skin Silicone comprising 2.5 grams of part A and 2.5 grams of part B is mixed. Alternatively, a thermoplastic elastomer such as Kraton CL2003X is used for its cost savings and its ability to be sutured. Approximately 20 microliters of fleshtone color is mixed into the silicone. The core 76 is inserted into the well 80 and the silicone mixture is poured into the mold base 72. The mixture is spread evenly up to a pour line making sure all the wells are filled. The top 74 is placed over the base 72 of the mold 70. Excess silicone mixture is cleaned away and the silicone inside the mold 70 is allowed to dry for approximately one hour under a heat lamp or for two hours without a heat lamp.

After the silicone mixture has dried, the top 74 is removed and the formed skin layer 40 is peeled and removed from the base 72. The core 76 is also removed. The integrally formed umbilical stalk 42 is inverted by passing it through a formed opening 92. Silicone adhesive is provided and delivered using a syringe to the inside of the tube of the umbilical stalk 42. One or more clamps and in one variation, three clamps, such as binder clips, are used to clamp the inverted umbilical stalk 42 closed and sealed to create a bellybutton shape having a star or Y-shaped closure as shown in FIG. 1 or 2. The bottom-most part of the umbilical stalk 42 is clamped to create a deep umbilicus as opposed to clamping closer to the skin layer bottom surface 64. The skin layer 40 is turned over and excess glue that may have seeped out of the umbilicus 42 is removed. The adhesive is allowed to dry for approximately one hour and the clamps are removed. In one variation, an umbilical shaft 42b is provided. The umbilical shaft 42b is tubular having a central lumen and made of a thin layer of white silicone that is approximately 1 mm thick. The umbilical shaft 42b is glued to the umbilical stalk 42a to extend the umbilicus deeper into the layers and create a more realistic look and feel. The umbilical shaft 42b is glued to the umbilical stalk 42a such that the lumens interconnect. The proximal end of the umbilical shaft 42b is place over the stalk 42a and glued thereto and the distal end of the umbilical shaft 42b is free. In another variation, the distal end of the umbilical shaft is glued or integrally formed with the peritoneum layer 58.

All of the layers are properly oriented in the same direction and aligned such that the apertures 66 and openings 68 are superimposed. Then, with the skin layer 40 inverted and the umbilical stalk 42a either alone or with an extended umbilical shaft 42b is passed through the circular aperture 66 of the fat layer 44 and through the elongate openings 68 of the anterior rectus sheath layer 46, the first rectus muscle layer 48, the second rectus muscle layer 50, and the third rectus muscle layer 52 and then through the circular apertures 66 of the posterior rectus sheath layer 54, the transversalis fascia layer 56 and the peritoneum layer 58 as shown in FIG. 5. In one variation, the umbilicus 42 is left meeting the peritoneum layer 58 or in another variation, the umbilicus 42 is attached with adhesive to the peritoneum layer 58 and yet in another variation, integrally molded with the peritoneum layer 58. The inferior epigastric vein and artery layer 60 is also included. This layer 60 can be formed as layer having a circular aperture 66 with embedded arteries and veins or simply comprise a pair of cylindrical silicone structures, one red and one blue, placed on one side of the midline and another pair of cylindrical silicone structures, one red and one blue in color, placed on the other side of the midline as shown in FIG. 4. The cylindrical silicone structures representing the epigastric veins and arteries are glued to at least one of the adjacent posterior rectus sheath layer 54 and the transversalis fascia layer 56. A price tag holder or other fastener can then be used to connect the layers together as shown in FIG. 5 with the umbilicus 42 shown protruding from the aperture 66 in the bottom-most peritoneum layer 58.

As can be seen in FIG. 5, the skin layer 50 and the peritoneum layer 58 is slightly larger than the other internal layers 44, 46, 48, 50, 52, 54, 56. In particular, the skin layer 50 and peritoneum layer 58 are larger by approximately 1.25 inches in length and width. Whereas the internal layers are approximately 6.5 inches long and 6 inches wide, the peritoneum layer 58 and skin layer 40 is approximately 8 inches long and 7.5 inches wide. These extra length and width portions are captured between the top and bottom frames of the support 14, pegs in one of the top or bottom frames are passed through apertures in the skin layer 40 formed by mold pegs 90. The peritoneum layer 58 may also include apertures for passing of frame pegs. The top frame and bottom frame are then heat staked together capturing the anatomical portion 12. The resulting model 10 is approximately 1.5 inches thick.

The first entry model 10 is then placed inside an opening in the top cover 22 of a laparoscopic trainer 20 and securely attached. Laparoscopic first entry procedures such as the ones discussed in the background of this specification are then practiced on the model 10 employing one or more of the trocar instruments described above creating first entry in any of the locations described above including first entry directly through the umbilicus. Another location for first entry could be within a half inch on either side of the midline. Although such first entry is not preferred, the practitioner will advantageously and quickly recognize a mistaken first approach when only the skin layer 42, the fat layer 44 and posterior rectus sheath 54 and peritoneum 58 layers are observed at the linea alba. The absence of a pink-colored first rectus muscle layer 48 should immediately alarm the practitioner during practice that penetration is at a wrong location. Another location for first entry penetration can take place at the left upper quadrant or right upper quadrant. As mentioned above, the left upper quadrant is different from the umbilicus region in that there are muscle layers. While penetrating at the upper right or left quadrants, the practitioner will observe the following layers: the skin layer 40, the fat layer 44, the anterior rectus sheath layer 46, the first rectus muscle layer 48, the second rectus muscle layer 50, the third rectus muscle layer 52, the posterior rectus sheath layer 54, the transversalis fascia layer 56 and the peritoneum layer 58.

The first entry model 10 of the present invention is particularly suited for laparoscopic procedures and may be employed with a laparoscopic trainer 20; however, the invention is not so limited and the first entry model 10 of the present invention can be used alone to practice first entry surgical procedures equally effectively.

Figure 11:
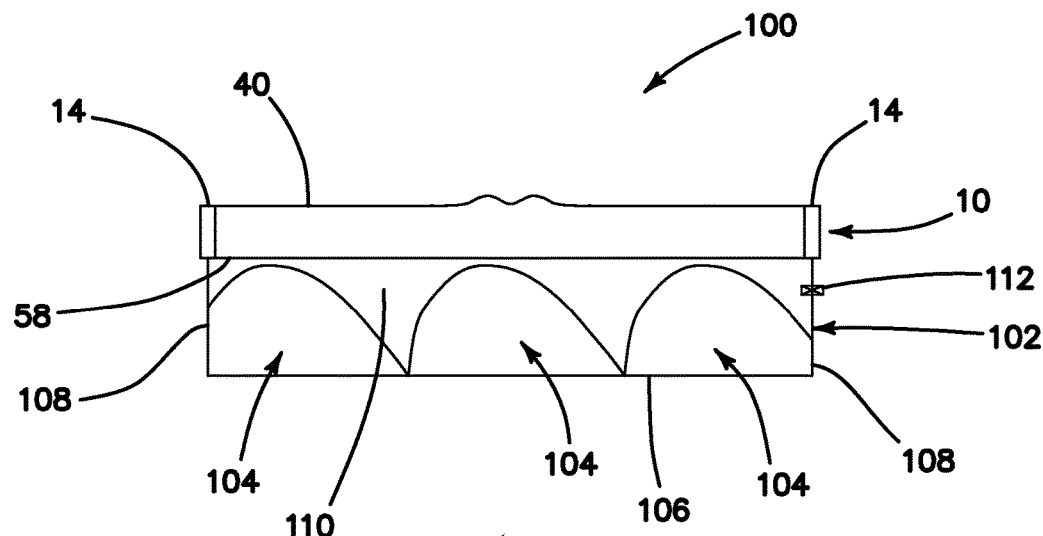
FIG. 11 is a cross-sectional, side view of a first entry model connected to an organ receptacle with organs according to the present invention.

Turning now to FIG. 11, a first entry system 100 will now be described wherein like parts are designated with like reference numerals. The first entry system 100 includes a first entry model 10 of the like described above. The first entry model 10 may include one or more of the layers described above and may or may not include openings 66, 68 and/or umbilicus 42. The first entry model 10 is connected to an organ receptacle 102. The organ receptacle 102 contains one or more live or simulated organs or tissue structures 104. The first entry system 100 may be inserted into a laparoscopic trainer 20 of the like described above. The first entry system 100 is configured to simulate insufflation of the abdominal space to provide a realistic insufflation training experience to the surgical trainee as will be described herein below.

The first entry model 10 includes at least a first simulated tissue layer 40 such as a skin layer 40 at a first end and a second simulated tissue layer 58 such as the peritoneum layer 58 at a second end. Between the first and second simulated tissue layers 40, 58, any number of additional simulated tissue layers and structures may be included as described above. The first entry model 10 includes a lower surface and an upper surface. Typically, the upper surface includes the top surface 62 of the skin layer 40 and the lower surface includes the outer-facing surface of the peritoneum layer 58.

The organ receptacle 102 includes a base 106 interconnected to one or more sidewalls 108 to define an interior 110 with an open top. The organs 104 are disposed inside the interior 110. The receptacle 102 need not have a defined base 106 and defined sidewalls 108. Instead, the base 106 may form an amorphous, bladder-like container with no distinguishable sides with the base 106 defining an interior 110 having an open top or mouth. In such a variation, the open top is sealingly connected to lower surface of the model 10 which typically is the peritoneum layer 58. Alternatively, the open top is connected to or captured between the frame elements of the support 14. In another variation, the receptacle 102 may include a radially outwardly extending flange around the open top. The flange is configured to be captured within the frame elements of the support 14 in order to be connected to the model 10. In another variation, the base 106 is rigid and substantially flat or planar suitable for supporting simulated organs 104 and connected to flexible sidewalls 108. In another variation, the receptacle 102 is at least one layer of elastomeric material having an upper surface and a lower surface defining a thickness. The layer comprises the receptacle 102. The upper surface of the layer is sealingly attached to the lower surface of the first entry model 10. It may be attached with or without adhesive. For example, without adhesive the receptacle 102 layer is capture within the frame support 14 about its perimeter and adjacent to the plurality of layers simulating the abdominal wall. Adhesive may be employed to sealingly attach to the lower surface of the model 10 such that a portion of unadhered or unattached layer is surrounded or encompassed by a portion of the layer that is attached creating an expandable separation or pocket between the model 10 and the layer of the receptacle 102. The wall/layer of the receptacle 102 may be made of transparent material.

The receptacle 102 is sealingly connected to the first entry model 10 such that the interior 110 of the receptacle 102 is sealed against the first entry model 10 leaving a central portion that is unsealed. The central portion or pocket is surrounded by the sealed portion. The receptacle 102 is a pocket. In one variation, the organ receptacle 102 is connected to the first entry model 10 such that the open top is sealed closed against the lowest simulated tissue layer 58. In another variation, the organ receptacle 102 is connected to the support or frame 14 of the first entry model 10. The organ receptacle 102 is connected such that the interior 110 is sealed from the exterior by at least a portion of the first entry model 10 and, in one variation, by the second simulated tissue layer 58 such that the second simulated tissue layer 58 closes or covers at least a portion of the open top of the receptacle 102.

In one variation, the receptacle 102 is completely enclosed and does not have an open top. In such a variation, at least one side surface of the receptacle 102 is adjacent to the first entry model 10 or the at least one side surface of the receptacle 102 itself comprises one of the layers of the first entry model 10 such as the second simulated peritoneum tissue layer 58. In this variation, the receptacle 102 may also include a flange element about its perimeter and configured to be capture within the frame elements of the support 14. In another variation, other fastening means for connecting the receptacle 102 to the model 102 are employed including but not limited to magnets, hook-and-loop type fastener, snaps, flanges, screws, pegs, and friction fit configurations.

The receptacle 102 can be made of any suitable material such as an elastic polymer, elastomer, polymer, silicone, Kraton, latex, rubber, gel, transparent gel, transparent silicone and the like. The receptacle 102 is elastic and can expand when inflated and contract is size when deflated. As such, the receptacle 102 is a balloon-like object. Simulated organs 104 that are placed inside the receptacle 102 can be made of any material such as silicone, Kraton, elastomer, polymer, plastic, rubber, hyrdrogel, mesh material and made include fillings of liquid, water, conductive material, filament and the like. In one variation, the simulated organs 104 include a two dimensional image attached to a three dimensional shape to provide a realistic appearance of the interior of the abdomen. In another variation, the simulated organs 104 comprise only a two dimensional image attached to the inner surface of the receptacle 102 that is smooth. The two dimensional image may be a picture, photograph, drawing of the interior of a patient including organs, tissues and colors. In yet another variation, the simulated organs 104 comprise a two dimensional image attached to the inner surface of the receptacle 102 that is contoured. It is understood that the simulated organs 104 are not limited to the depiction or simulation of organs but may include tissues in general, partial organs and/or colorations that are not readily identifiable as organs or tissue but depict the color of blood, fat, muscle, and/or tumors and the like.

Furthermore, upon sealing the receptacle 102 to the first entry model 10 or prior to attachment of a closed receptacle 102, a negative pressure is created within the interior 110 of the receptacle 102 relative to the exterior. A valve 112 may be provided across the receptacle 102 to create a vacuum inside the receptacle 102. The valve 112 is configured to be connectable to a vacuum source, for example, a mechanical, electro-mechanical and/or hand pump and the like. The receptacle 102 is configured such that with the application of negative pressure, the volume of the interior 110 is reduced as shown in FIG. 11. The reduction in volume of the interior 110 is accomplished by making at least the sidewalls of receptacle 102 from an elastic or flexible plastic material such that the sides of the receptacle 102 are drawn up closer to the first entry model 10, and, in particular, closer to the second simulated tissue layer 58 when a vacuum is applied. Of course, the entire receptacle 102 can be made of an elastic, flexible plastic, or balloon-like material such that the entirety of the receptacle 102 is permitted to be drawn closer to the first entry model 10 in an undeformed condition or upon application of negative pressure. Alternatively, only the sidewalls 108 are retracted under negative pressure with the base 106 being substantially rigid relative to the sidewalls 108. In such a variation, the sidewalls 108 are configured to contract resulting in the base 106 being pulled closer to the first entry model 10 under a vacuum. In any variation, as a result of the application of negative pressure, the simulated organs 104 that are located inside the receptacle 102 will also be drawn closer to the first entry model 10 along with the base 106 as shown in FIG. 11. Hence, the distance between the second simulated tissue layer 58 and the base 106 is reduced.

Figure 12:
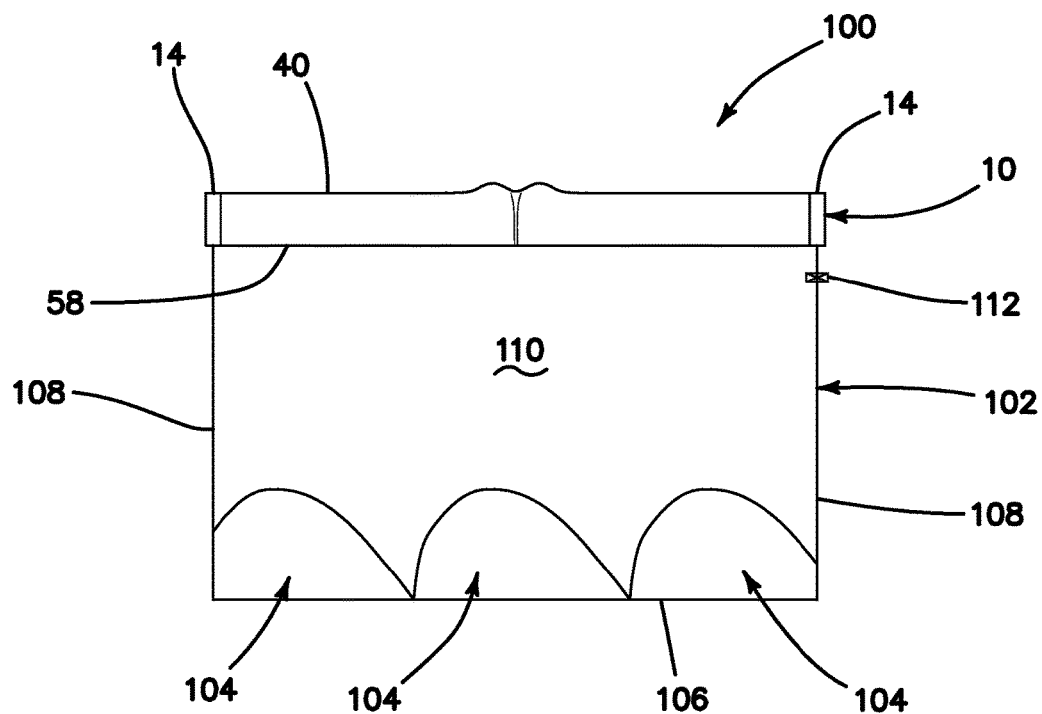
FIG. 12 is a cross-sectional, side view of a first entry model connected to an organ receptacle with organs according to the present invention.

Since the first entry model 10 is located above the organ receptacle 102, penetration of the first simulated tissue layer 40 by a trocar or other instrument will be followed by penetration of the second simulated tissue layer 58 with continued advancement of the trocar or other instrument. Such penetration will include penetration of any additional intervening layers such as any one or more of the fat layer 44, anterior rectus sheath 46, second rectus muscle layer 48, second rectus muscle layer 50, third rectus muscle layer 52, posterior rectus sheath layer 54, transversalis fascia layer 56, and inferior epigastric vein and artery layer 60 that may be part of the model 10. Upon penetration of the second simulated tissue layer 58 or lowest layer, the vacuum will be broken and the pressure of the interior 110 will equalize with the exterior pressure either through the puncture itself or through an aperture in the distal tip of the trocar or other instrument. The FIOS® trocar manufactured by Applied Medical Resources, Inc. in California advantageously includes a distally located vent hole in the penetrating, transparent tip of the trocar which provides fluid communication between the interior 110 of the receptacle 102 and the exterior or other fluid source. In one variation, the trocar or other instrument includes a stopcock valve at the proximal end of the trocar which the user would open in order to equalize pressure with the interior 110. When the seal of the receptacle 102 is broken by the penetrating trocar or other instrument, or otherwise the pressure is equalized, such as by the penetration of the receptacle 102, the volume of the interior 110 will increase. As the volume of the interior 110 increases, the flexible or elastic sidewalls 102 and/or base 106 will unfurl and the distance between the base 106 and the first entry model 10 will increase. A camera such as a laparoscope disposed inside the trocar or other instrument, will provide to the user a live visualization of the penetration via a video feed connected to a display monitor 34. The penetration of the seal and/or equalization of the pressure will provide a dynamic visual to the user of the organs 104 appearing to drop relative to the first entry model 10 to an insufflated condition of the receptacle 102 shown in FIG. 12. Hence, the present invention provides a simulation of insufflation without the use of insufflation gas.

If the receptacle 102 includes an open top or mouth connected to the model 10 or if the receptacle 102 is an enclosed container, a negative pressure may be generated inside the interior 110 across a valve 112 just prior to demonstration or at the factory before shipment. The user may attach a pump to remove air and create the first configuration. In one variation, the valve 112 is a check valve permitting flow in one direction. In another variation, the valve 112 is a one-way pressure valve that opens to release air from the interior of the receptacle 102 when the receptacle 102 is subjected to sufficient compression pressure to open the valve. When the pressure on the receptacle is released, the valve 112 closes. Hence, prior to use, the user can squeeze the receptacle to release air from the interior of the receptacle 102 across the one-way pressure valve which closes and seals the receptacle 102 after the squeezing on the receptacle 102 is stopped. With the excess air removed from the receptacle 102 the interior volume of the receptacle 102 is reduced from a first volume to a second volume. The sidewall of the receptacle 102 is scrunched around the simulated organs 104 inside the receptacle 102. When the receptacle 102 is punctured, the volume of air in the receptacle returns to the first volume which is larger than the second volume. As the volume of the interior increases, typically under the influence of gravity. The weight of the receptacle 102 and/or simulated organs 104 will be pulled by gravity downwardly away from the model 10. In such a configuration, the receptacle 102 is suspended or hanging from the model 10 with space beneath the receptacle 102 such as inside the laparoscopic trainer 20. The expansion in volume of the interior of the receptacle 102 is a result of stretching of the sidewall of the receptacle 102 or by an unfoldment, unfurling, unwrinkling of the receptacle 102 sidewall in one or more locations. Because the simulated organs 104 are heavier than the receptacle 104, the simulated organs 104 will drop under the influence of gravity from a prior position being drawn up closer to the model 10. The puncture permits air to enter the interior 110 of the receptacle 102 and the receptacle 102 expands downwardly assuming a natural configuration. In essence, air is removed or evacuated from the receptacle 102, for example via a one way valve or other opening, creating a situation wherein the contents of the receptacle 102 are held in place close to the model 10 or lowermost layer of simulated tissue 58 until the user creates an air passageway into the interior 110 of the receptacle 102 at which point the interior opens due to the force of gravity acting on the receptacle and/or simulated organs 104. The air passageway into the interior 110 of the receptacle 102 is created by the insertion of a trocar across the model 10 and into the interior of the receptacle 102 in a simulated medical procedure. The receptacle 102 may include a zipper for accessing the interior 110 for the customized selection and placement of simulated organs 104 inside the receptacle 102 by the user. The simulated organs 104 may be pre-loaded into the receptacle 102 or loaded by the user just prior to use. Also, the pressure differential inside the receptacle 102 may be created by the user on site using a various pumps or, alternatively, the receptacle 102 is sealed and shipped in a ready-to-use state to the user.

In another variation of the first entry system 100, no vacuum or pressure differential across the receptacle 102 is employed. Instead, actual insufflation fluid is delivered via the penetrating trocar or other instrument at the penetration site, or other location, into the interior 110 of the receptacle 102. The penetrating trocar is connected at the proximal to a source of fluid such as air under pressure to be delivered out through a vent-hole located in the distal end of the trocar after penetration has occurred. The source of fluid may be, for example, a gas tank, a balloon filled with air, an electrical or mechanical pump such as a hand pump. In such a variation, the receptacle 102 is made of balloon-like material. The receptacle 102 is configured such that the sidewalls 108 and/or base 106 expand under the insufflation pressure from a first small-volume condition to an enlarged volume insufflated condition. In such a variation, the volume of the interior 110 of the receptacle 102 is increased. This increase in volume can be created by expansion of the receptacle walls such as by the stretching of the elastic material as in a balloon-like configuration or by an unfoldment, unfurling, unwrinkling of the receptacle 102 sidewall in one or more locations. The change in volume provides the visual of a simulated insufflation to the trainee observing the procedure via the video monitor 34.

In yet another variation of the first entry system 100, a valve 112 is provided across the receptacle 102 such that pressure is equalized or insufflation fluid is provided via the valve instead of via the trocar or other instrument. The valve can be opened/closed by the user or other operator to increase the volume of the receptacle 102 to simulate insufflation.

In another variation, the distance between the base 106 and the first entry model 10 is increased by mechanical means such as hydraulics, levers or balloons upon penetration of the first entry model 10 and activated automatically upon penetration of the second simulated tissue layer 58 or activated manually by the user or teacher as desired. In one variation, the receptacle 102 does not contain the simulated organs 104 inside the interior 110. Instead, the simulated organs 104 are placed on the exterior surface of the receptacle 102 next to the model 10 such that the simulated organs 104 are located between the receptacle 102 and the model 10. In such a variation, the receptacle 102 such as a balloon includes an expanded configuration such that the outer surface of the receptacle 102 pushes and locates the simulated organs 104 into juxtaposition to the lower surface of the model 10. When at least one information is received that the lower surface of the model 10 such as the peritoneum layer 58 has been surgically penetrated by the trocar or other surgical instrument in the performance of a surgical procedure, the at least one information is communicated to a processor that instructs a the mechanical or electro-mechanical deflation of the receptacle 102 to occur. The deflating receptacle 102 moves the simulated organs 104 that are located on the outer surface of the receptacle 102 downwardly such that the visual that is received from the vantage point of the penetrating instrument, such as an optical obturator/trocar, is receding simulated organs or simulated organs that moving distally away from the penetrating instrument or otherwise away from the model 10. In such a variation, the simulated organs 104 may be connected by adhesive to the outer surface of the receptacle 102. In another variation of the simulated organs 104 residing exterior to the receptacle 102, the simulated organs 104 include a two-dimensional image with or without a three-dimensional underlay. For example, an image of simulated organs is provided by an image attached to the exterior of the receptacle 102 such that upon deflation of the receptacle the image moves distally away from the model 10. In another variation, the image is attached to a rigid flat or contoured surface that is attached to the exterior surface of the receptacle 102.

In another variation, the negative pressure of the interior 110 relative to the exterior may be restored either through a valve 112 across the receptacle 102 or through the inserted trocar in order to simulate a loss of pneumoperitoneum during the course of a procedure. The restoration of negative pressure may be activated by a teacher while the student is practicing surgical procedures to train the student on how to handle the loss of pressure during a surgical procedure.

In another variation of the first entry system 100, the first entry system 100 includes a penetrable tissue structure comprising a plurality of layers that simulates an abdominal wall such as the first entry model 10 or anatomical portion 12 described above. The system 100 includes a receptacle connected to the penetrable tissue structure. The receptacle 102 includes a wall that is configured as at least one layer of elastomeric material. The at least one layer comprises the receptacle. The receptacle layer has an upper surface and a lower surface. The receptacle layer is attached to the penetrable tissue structure such that the upper surface of the receptacle layer is in juxtaposition adjacent to the penetrable tissue structure. The upper surface of the receptacle layer is sealingly attached to the lower surface of the penetrable tissue structure. It may be attached with or without adhesive. For example, without adhesive the receptacle 102 layer is captured along its perimeter within the frame support 14 between the frame elements described above. As such the perimeter and adjacent to the plurality of layers simulating the abdominal wall. Adhesive may be employed to sealingly attach the receptacle layer to the lower surface of the penetrable tissue structure such that a portion of unadhered or unattached receptacle layer is surrounded or encompassed by a portion of the receptacle layer that is attached creating an expandable separation or at least one pocket between penetrable tissue structure and the receptacle layer. The receptacle layer may be made of transparent material such as clear gel, transparent silicone, or any transparent elastomer including rubber, polymer and the like. Adhesive may be employed to sealingly connect the receptacle layer to the penetrable tissue structure in the similar manner to create at least one pocket. The receptacle layer is sealed against the penetrable tissue structure leaving a central portion that is unsealed. The unsealed central portion of the receptacle layer is surrounded by the portion of the receptacle layer that is sealed to the penetrable tissue structure. The unseal central portion forms a pocket that is seal so as to prevent the passage of fluid including gas into and out of the central portion. As such, deliberate introduction of fluid under pressure into the central portion will expand and inflate the elastomeric wall which will provide a visual to the user that simulates abdominal insufflation. The receptacle 102 is a pocket. The system includes at least one tissue simulation of the like described above including but not limited to two-dimensional constructs such as images or three-dimensional structures that simulate tissue, organs with textures, contours and colors. The tissue simulation is located inside the receptacle pocket may include simulated vasculature, fat, organs, intestines etc. In another variation, the tissue simulation is integrally formed with the receptacle layer. For example, the receptacle layer is formed from a plurality of layers with each layer having the desired size and shape and transparency to simulate tissues and organs encountered in the abdomen of a human being. The tissue simulation may or may not be attached to the receptacle layer/wall. In one variation, the tissue simulation is attached to the lower surface of the receptacle layer. In such a variation, the attached tissue simulation is visible through a transparent receptacle layer. The receptacle layer has a first configuration and a second configuration. While in the first configuration of the receptacle, the tissue simulation inside the receptacle is located proximally to the simulated tissue structure relative to the second configuration wherein while in the second configuration at least part of the tissue simulation inside the receptacle is located distally from simulated tissue structure relative to the first configuration. Fluid is transferable into the receptacle pocket to convert the receptacle from a first configuration to a second configuration. This can be accomplished in several ways. One way is removing air from the pocket creating a vacuum or partial vacuum such that the receptacle pocket layer is withdrawn closer to the penetrable simulated tissue structure. When the penetrable simulated tissue structure is penetrated with a distal tip of a surgical instrument such as the distal tip of an optical obturator, the vacuum is release and pressure is equalized causing the receptacle layer/wall to sag or move away from the penetrable simulated tissue structure especially under weight of the tissue simulations located in the receptacle. In another variation, the second configuration is achieved by delivering fluid such as air under pressure directly through the tip of the penetrating surgical device such as an optical obturator having a vent hole in the tip at the distal end and a fluid port at the proximal end for connecting to a source of fluid under pressure. The fluid port includes a luer-lock for turning on and off the insufflation gas. Fluid may be delivered via a mechanical hand pump connected to the fluid port of the obturator. Fluid may also be delivered from an inflated bladder such as a balloon or other canister. The fluid source is connected via tubing to the fluid port on the obturator. The fluid port is opened and fluid from a source is delivered into the obturator and out the vent hole in the tip and with the tip localized inside the pocket fluid is delivered into the pocket. Since the receptacle layer is elastic, it will expand with the delivery of gas moving the simulation tissue away from the penetrable simulated tissue structure and as a result providing a visual from the viewpoint of the obturator that simulates insufflation of a real abdominal cavity. In one variation, the first entry system 100 described above is configured as a hand-held model for sales demonstration purposes as well as for training first entry surgical techniques. The tubing that connects the fluid source to the fluid port may serve as a hand piece or handle for holding and carrying the system. The hand-held model is also sized and configured such as with a handle to be easily held in one hand and easily turned over. Therefore, the system is ergonomically designed and is approximately 3-6 inches in diameter. The penetrable simulated tissue structure and receptacle are contained inside a support with frame elements exposing the proximal skin side of the abdominal wall as well as the distal receptacle pocket layer that is transparent. As mentioned previously, the tissue simulation may include images of simulated or actual vasculature and the like disposed on the pocket. The salesperson or practitioner can employ an obturator that is connected to a fluid source and begin penetrating the system from the skin-side or top side of the model. With continued penetration into the plurality of layers, the user may then turn the fluid port on to allow fluid to flow into the obturator. If the vent hole in the tip of the obturator is covered with the layers of the penetrable tissue structure as it is making its way through the layers, fluid will not flow and the receptacle layer will not expand. Only when the final layer, such as the peritoneum layer, in the penetrable tissue structure is penetrated in the location of the pocket will the receptacle layer will expand as fluid from the fluid source is now free to flow into the pocket without being obstructed by tissue layers. The user will, thereby, be able to demonstrate and teach how much penetration with the obturator is required to effect insufflation. The observer or student will quickly see the transparent receptacle layer expand providing a visual indication that insufflation is taking place. The point of penetration can also be noted when the hand-held model is easily turned upside-down to see if any of the tissue simulation has been contacted with the distal tip when entering the pocket. The system further includes plugs such as dowel pins sized to fit into the openings created by any previous penetrations so that the system is reusable and subsequent multiple penetrations and demonstrations are possible. Also, one of the layers, preferably one simulating the adipose fat layer, inside the penetrable simulated tissue structure is made of self-sealing foam to help plug the previous penetrations making the structure reusable. In one variation, the tubing connecting the fluid source to the obturator includes a fluid flow regulator to adjust the amount and flow rate of fluid entering the obturator. The flow-regulator may include a clip-type flow restrictor having one or more settings such as for low, medium and high flow rates.

It is understood that various modifications may be made to the embodiments of the first entry model 10 and/or first entry system 100 disclosed herein. Therefore, the above description should not be construed as limiting, but merely as exemplifications of preferred embodiments. Those skilled in the art will envision other modifications within the scope and spirit of the present disclosure.

We claim:

1. A surgical training device, comprising:
   a laparoscopic trainer having a cavity and a floor for the cavity;
   a penetrable simulated tissue structure having an upper surface and a lower surface and comprising at least one layer that simulates a tissue layer;
   a receptacle connected to the simulated tissue structure; the receptacle having a wall defining an interior of the receptacle;
   one or more simulated organs located in the interior of the receptacle; the one or more simulated organs being configured to be located proximate to the simulated tissue structure; and
   a support configured to connect the receptacle to the laparoscopic trainer such that the receptacle is suspended above the floor of the cavity;
   wherein the surgical training device is configured such that penetration of one or more of the simulated tissue structure and receptacle results in at least part of the one or more simulated organs inside the receptacle to translate distally away from the simulated tissue structure to simulate surgical insufflation of an abdominal cavity.

2. The surgical training device of claim 1 wherein the receptacle includes a top opening; the receptacle being connected to the penetrable simulated tissue structure such that the perimeter of the opening is sealed against the penetrable simulated tissue structure to prevent the transfer of fluid into and out of the interior of the receptacle.

3. The surgical training device of claim 1 wherein the wall of the receptacle completely surrounds the one or more simulated organs; the wall defining an exterior of the receptacle; and further including a valve located across the wall of the receptacle to provide fluid communication across the exterior and interior of the receptacle.

4. The surgical training device of claim 3 wherein the valve is a check-valve or a one-way pressure valve.

5. The surgical training device of claim 1 wherein the simulated tissue structure includes a plurality of substantially planar layers configured to simulate an abdominal wall.

6. The surgical training device of claim 1 wherein the simulated tissue structure is penetrable with a blunt surgical instrument.

7. The surgical training device of claim 1 wherein the receptacle is provided with a negative pressure inside the interior of the receptacle relative to the exterior of the receptacle.

8. The surgical training device of claim 7 wherein penetration of the receptacle releases the negative pressure.

9. A surgical training device, comprising:
   a laparoscopic trainer having a cavity and a floor for the cavity;
   a penetrable simulated tissue structure configured to simulate an abdominal wall;
   a receptacle connected to the tissue structure; the receptacle having a wall defining an interior and an exterior of the receptacle; the receptacle having a first configuration and a second configuration;
   at least one tissue simulation located inside the receptacle; and
   a support configured to connect the receptacle to the laparoscopic trainer such that the receptacle is suspended above the floor of the cavity;
   wherein while in the first configuration of the receptacle, the at least one tissue simulation inside the receptacle is located proximate to the simulated tissue structure relative to the second configuration wherein while in the second configuration at least part of the tissue simulation inside the receptacle is located distally from simulated tissue structure relative to the first configuration; and
   wherein fluid is transferable into the receptacle to convert the receptacle from a first configuration to a second configuration.

10. The surgical training device of claim 9 wherein transfer of fluid into the receptacle causes at least part of the at least one tissue simulation to translate from away from the simulated tissue structure.

11. The surgical training device of claim 9 wherein the receptacle has a first volume of fluid located inside the receptacle when in the first configuration and a second volume of fluid located inside the receptacle when in the second configuration;
    and the second volume of fluid is greater than the first volume of fluid.

12. The surgical training device of claim 9 further including a valve across the wall of the receptacle for fluidic communication between the interior and the exterior of the cavity.

13. The surgical training device of claim 9 wherein the wall of the receptacle is elastic and transfer of fluid into the receptacle causes the receptacle wall to stretch.

14. The surgical training device of claim 13 wherein the wall of the receptacle is a layer of elastomeric material having an upper surface and a lower surface; the layer is attached to seal to a lower surface of the penetrable tissue structure such that a portion of the attached wall encompasses a portion of wall that is not attached to the penetrable simulated tissue structure.

15. The surgical training device of claim 9 wherein the wall of the receptacle is transparent.

16. The surgical training device of claim 9 wherein the penetrable simulated tissue structure includes a plurality of simulated tissue layers arranged in juxtaposition with each other; the simulated tissue layers include a simulated skin layer located above the remaining layers; each of the remaining layers having an opening extending through the layer; the simulated skin layer having a top surface and a bottom surface; the top surface of the simulated skin layer defines a first side of the simulated tissue structure; a tubular structure having a proximal end and a distal opening at a distal end; the distal end of the tubular structure extending through one or more openings in the remaining layers.

17. A method for simulating surgical insufflation comprising the steps of:
    providing a model comprising a penetrable artificial tissue structure configured to simulate an abdominal wall; the model including a receptacle having a wall connected to the artificial tissue structure; the model including at least one tissue simulation disposed inside the receptacle and located proximally proximate to the artificial tissue structure;
    providing a laparoscopic trainer having a cavity and a floor for the cavity;
    suspending the model above the floor of the cavity inside the laparoscopic trainer;
    moving an optical surgical obturator through the artificial tissue structure and into the receptacle;

observing the at least one tissue simulation inside the receptacle through the distal end of the optical obturator;

moving the at least one tissue simulation from a position proximal to the artificial tissue structure to a position relatively distal to the artificial tissue structure to simulate insufflation of an abdominal cavity.

18. The method of claim 17 further including the steps of:

creating a vacuum inside the receptacle; and wherein the step of moving the at least one tissue simulation includes breaking the vacuum inside the receptacle.

19. The method of claim 17 further including the steps of:

providing a receptacle with an elastic wall;

transferring fluid into the receptacle and wherein the step of moving the at least one tissue simulation includes expanding the elastic wall of the receptacle.

* * * * *